US006391603B1

(12) United States Patent
Pompejus et al.

(10) Patent No.: US 6,391,603 B1
(45) Date of Patent: May 21, 2002

(54) GENES OF PURINE BIOSYNTHESIS FROM ASHBYA GOSSYPII AND THE USE THEREOF IN MICROBIAL RIBOFLAVIN SYNTHESIS

(75) Inventors: Markus Pompejus, Waldsee; Harald Seulberger, Neuhofen; Hans Wolfgang Höffken, Ludwigshafen, all of (DE); Jose Luis Revuelta Doval, Salamanca (ES); Alberto Jimenez, Salamanca (ES); Maria Angeles Santos Garcia, Salamanco (ES)

(73) Assignee: BASF Aktiengesellschaft, Lugwigshafen (DE)

( * ) Notice: Subject to any disclaimer, the term of this patent is extended or adjusted under 35 U.S.C. 154(b) by 0 days.

(21) Appl. No.: 09/212,247

(22) Filed: Dec. 16, 1998

(30) Foreign Application Priority Data

Dec. 23, 1997 (DE) .......................... 197 57 755

(51) Int. Cl.[7] ................................ C12N 9/10
(52) U.S. Cl. ...................................... 435/193
(58) Field of Search .................. 435/193, 194

(56) References Cited

U.S. PATENT DOCUMENTS 5,821,090 A   10/1998   Doval et al. ................. 435/88

FOREIGN PATENT DOCUMENTS

EP   405370   1/1991

OTHER PUBLICATIONS

GenBank Accession AAA75450 "glutamine phosphoribosylpyrophosphate amidotransferase" Submitted by Marsh et al, Sep. 17, 1995.*

Voet et al., *Biochemistry*, 1994, p/743–771.

Zalkin et al., *Progress in Nucleic Acid Research & Molecular Biol*, vol. 42, 1992, pp.259–287.

Christopherson et al., *Med. Res. Reviews*, vol. 10, No. 4, pp. 505–548, 1990.

Smith, *Current Opinion in Structural Biology*, vol. 5, No. 1, pp. 752–757, 1995.

Simmonds, *Biochem. Soc. Transact.*, vol. 23, pp. 877–902, 1995.

* cited by examiner

*Primary Examiner*—Ponnathapu Achutamurthy
*Assistant Examiner*—David J. Steadman
(74) *Attorney, Agent, or Firm*—Keil & Weinkauf

(57) ABSTRACT

Genes of purine biosynthesis from *Ashbya gossypii* are used in microbial riboflavin synthesis.

2 Claims, 2 Drawing Sheets

Figure 1:
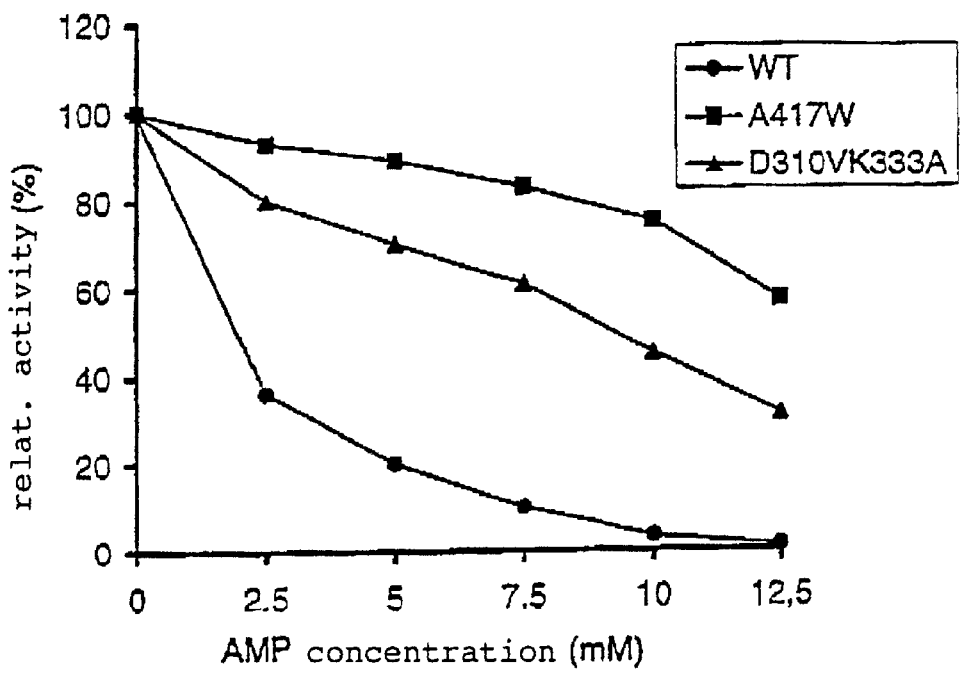
Figure 1:
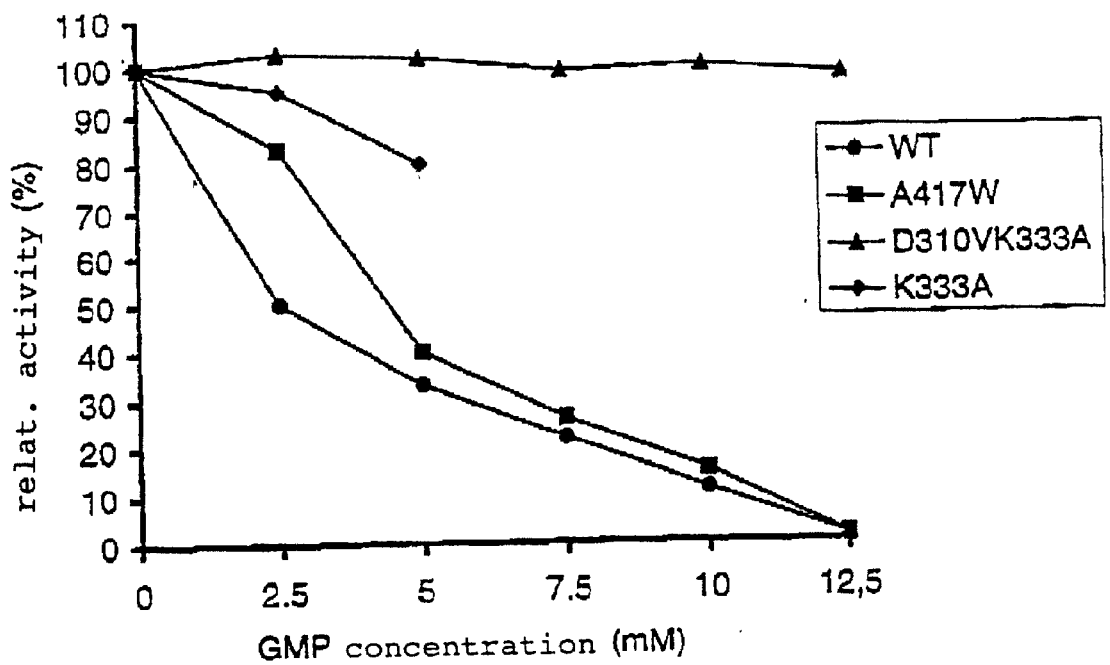

Inhibition of wild-type and mutagenized KPRS by ADP

SEQUENCE LISTING

```
(1) GENERAL INFORMATION:

(iii) NUMBER OF SEQUENCES: 21

(2) INFORMATION FOR SEQ ID NO: 1:

(i) SEQUENCE CHARACTERISTICS:
        (A) LENGTH: 1911 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: 5'UTR
        (B) LOCATION: 1..625

(ix) FEATURE:
        (A) NAME/KEY: CDS
        (B) LOCATION: 626..1582

(ix) FEATURE:
        (A) NAME/KEY: 3'UTR
        (B) LOCATION: 1583..1911

(xi) SEQUENCE DESCRIPTION: SEQ ID NO: 1:

GGTAGTCGCT CATCGACAGA CACAATCGCG TGTTCTCTCT GAATCGTCCA T TGGGTGTCA      60
```

```
GCATCCTGAT CGCGGGCGGA TGGAATGGGT AATCATTAGG AAACACCAAT G TCCCATGGT        120

ATTGTCCGTC CTCGTATGGT GTCTCAGGAG GACCCGTGAT CACGTAGTGC C ACACCAGGA        180

TATTGTCTTC CTTTGGTGCT GCCACGATGT AGGGCGGGGG GTTCTCGGTC A TCATTTTGT        240

ACTCCTTTGA GAGCCGCTTG TACGCCTGTC TTGATGCCAT CTTGCCTACT A TTAGTTTCT        300

CACCACTTCC CGCCAAACAA TCTGCACTTT ACGAGCGCTA TCTATCCCTC G GGTCGCTCT        360

AGTTGATTAT TGGCGAAACT GATAGTTCAG GTACTTCCAT GATGCGGTCA T ATCCACGTA        420

TGTGATCACG TGATCATCAG CCATGCTGCC AGCTCACGGG CCTGCCTACA C TATTGGAGG        480

CTCTGTGAGT CATGATTTAT TGCATATCAA GCCCAGATAG TCGTTGGGGA T ACTACCGTT        540

GCCGCGATGA GCTCCGATAT TAAGTTGTAG CCAAAAATTT TAACGGATGA C TTCTTAACA        600

GTTATTGACG CCGCAATCCT ACGCC ATG TCG TCC AAT AGC ATA AAG CTG CTA           652
                            Met Ser Ser Asn Ser Ile Lys Leu Leu
                             1                5

GCA GGT AAC TCG CAC CCG GAC CTA GCT GAG A AG GTC TCC GTT CGC CTA          700
Ala Gly Asn Ser His Pro Asp Leu Ala Glu L ys Val Ser Val Arg Leu
 10              15                  20                      25

GGT GTA CCA CTT TCG AAG ATT GGA GTG TAT C AC TAC TCT AAC AAA GAG          748
Gly Val Pro Leu Ser Lys Ile Gly Val Tyr H is Tyr Ser Asn Lys Glu
             30                  35                      40

ACG TCA GTT ACT ATC GGC GAA AGT ATC CGT G AT GAA GAT GTC TAC ATC          796
Thr Ser Val Thr Ile Gly Glu Ser Ile Arg A sp Glu Asp Val Tyr Ile
         45                  50                      55

ATC CAG ACA GGA ACG GGG GAG CAG GAA ATC A AC GAC TTC CTC ATG GAA          844
Ile Gln Thr Gly Thr Gly Glu Gln Glu Ile A sn Asp Phe Leu Met Glu
     60                  65                      70

CTG CTC ATC ATG ATC CAT GCC TGC CGG TCA G CC TCT GCG CGG AAG ATC          892
Leu Leu Ile Met Ile His Ala Cys Arg Ser A la Ser Ala Arg Lys Ile
 75              80                      85

ACA GCG GTT ATA CCA AAC TTC CCT TAC GCA A GA CAA GAC AAA AAG GAC          940
Thr Ala Val Ile Pro Asn Phe Pro Tyr Ala A rg Gln Asp Lys Lys Asp
 90              95                  100                     105

AAG TCG CGA GCA CCG ATA ACT GCC AAG CTG G TG GCC AAG ATG CTA GAG          988
Lys Ser Arg Ala Pro Ile Thr Ala Lys Leu V al Ala Lys Met Leu Glu
             110                 115                     120

ACC GCG GGG TGC AAC CAC GTT ATC ACG ATG G AT TTG CAC GCG TCT CAA          1036
Thr Ala Gly Cys Asn His Val Ile Thr Met A sp Leu His Ala Ser Gln
             125                 130                     135

ATT CAG GGT TTC TTC CAC ATT CCA GTG GAC A AC CTA TAT GCA GAG CCG          1084
Ile Gln Gly Phe Phe His Ile Pro Val Asp A sn Leu Tyr Ala Glu Pro
         140                 145                     150

AAC ATC CTG CAC TAC ATC CAA CAT AAT GTG G AC TTC CAG AAT AGT ATG          1132
Asn Ile Leu His Tyr Ile Gln His Asn Val A sp Phe Gln Asn Ser Met
 155                 160                     165

TTG GTC GCG CCA GAC GCG GGG TCG GCG AAG C GC ACG TCG ACG CTT TCG          1180
Leu Val Ala Pro Asp Ala Gly Ser Ala Lys A rg Thr Ser Thr Leu Ser
170             175                 180                     185

GAC AAG CTG AAT CTC AAC TTC GCG TTG ATC C AC AAA GAA CGG CAG AAG          1228
Asp Lys Leu Asn Leu Asn Phe Ala Leu Ile H is Lys Glu Arg Gln Lys
             190                 195                     200

GCG AAC GAG GTC TCG CGG ATG GTG TTG GTG G GT GAT GTC GCC GAC AAG          1276
Ala Asn Glu Val Ser Arg Met Val Leu Val G ly Asp Val Ala Asp Lys
             205                 210                     215

TCC TGT ATT ATT GTA GAC GAC ATG GCG GAC A CG TGC GGA ACG CTA GTG          1324
Ser Cys Ile Ile Val Asp Asp Met Ala Asp T hr Cys Gly Thr Leu Val
         220                 225                     230
```

-continued

```
AAG GCC ACT GAC ACG CTG ATC GAA AAT TGT G CG AAA GAA GTG ATT GCC      1372
Lys Ala Thr Asp Thr Leu Ile Glu Asn Cys A la Lys Glu Val Ile Ala
    235                 240                 245

ATT GTG ACA CAC GGT ATA TTT TCT GGC GGC G CC CGC GAG AAG TTG CGC      1420
Ile Val Thr His Gly Ile Phe Ser Gly Gly A la Arg Glu Lys Leu Arg
250                 255                 260                 265

AAC AGC AAG CTG GCA CGG ATC GTA AGC ACA A AT ACG GTG CCA GTG GAC      1468
Asn Ser Lys Leu Ala Arg Ile Val Ser Thr A sn Thr Val Pro Val Asp
                270                 275                 280

CTC AAT CTA GAT ATC TAC CAC CAA ATT GAC A TT AGT GCC ATT TTG GCC      1516
Leu Asn Leu Asp Ile Tyr His Gln Ile Asp I le Ser Ala Ile Leu Ala
            285                 290                 295

GAG GCA ATT AGA AGG CTT CAC AAC GGG GAA A GT GTG TCG TAC CTG TTC      1564
Glu Ala Ile Arg Arg Leu His Asn Gly Glu S er Val Ser Tyr Leu Phe
        300                 305                 310

AAT AAC GCT GTC ATG TAGTGCTGTC AGTGGCAGAT GCATGATC GC TGGCCTAATT      1619
Asn Asn Ala Val Met
    315

ATCTGTGTAA GTTGATACAA TGCAGTAAAT ACAGTACATA AAACTGAATG T TTTTCACTT    1679

AGGGGTGCTT TGTTGTTCTG ATAGCGTGTG TGCGAATTTG GAGGTGAAAG T TGAACATCA    1739

CGTAATGAAT ACAAACAAGA TTGCACATTA GGAAAAGCGA TAAATTATTT A TTATTTGCA    1799

ACTGGCCTTT GAGCGTTTAA GCCTGAACAT TTTTGCCCTT TTGTTTGACC G TACCGTTAT    1859

CACTCGTCCT TATATATGGC TATCCTTCTC TTCCGGAACT TCTTCGAGCG T A            1911
```

(2) INFORMATION FOR SEQ ID NO: 2:

(i) SEQUENCE CHARACTERISTICS:
        (A) LENGTH: 318 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Ser Asn Ser Ile Lys Leu Leu Ala G ly Asn Ser His Pro Asp
 1               5                  10                  15

Leu Ala Glu Lys Val Ser Val Arg Leu Gly V al Pro Leu Ser Lys Ile
            20                  25                  30

Gly Val Tyr His Tyr Ser Asn Lys Glu Thr S er Val Thr Ile Gly Glu
        35                  40                  45

Ser Ile Arg Asp Glu Asp Val Tyr Ile Gly l n Thr Gly Thr Gly Glu
    50                  55                  60

Gln Glu Ile Asn Asp Phe Leu Met Glu Leu L eu Ile Met Ile His Ala
65                  70                  75                  80

Cys Arg Ser Ala Ser Ala Arg Lys Ile Thr A la Val Ile Pro Asn Phe
                85                  90                  95

Pro Tyr Ala Arg Gln Asp Lys Lys Asp Lys S er Arg Ala Pro Ile Thr
            100                 105                 110

Ala Lys Leu Val Ala Lys Met Leu Glu Thr A la Gly Cys Asn His Val
        115                 120                 125

Ile Thr Met Asp Leu His Ala Ser Gln Ile G ln Gly Phe Phe His Ile
    130                 135                 140

Pro Val Asp Asn Leu Tyr Ala Glu Pro Asn I le Leu His Tyr Ile Gln
145                 150                 155                 160

His Asn Val Asp Phe Gln Asn Ser Met Leu V al Ala Pro Asp Ala Gly
                165                 170                 175
```

```
Ser Ala Lys Arg Thr Ser Thr Leu Ser Asp Lys Leu Asn Leu Asn Phe
            180                 185                 190

Ala Leu Ile His Lys Glu Arg Gln Lys Ala Asn Glu Val Ser Arg Met
        195                 200                 205

Val Leu Val Gly Asp Val Ala Asp Lys Ser Cys Ile Ile Val Asp Asp
    210                 215                 220

Met Ala Asp Thr Cys Gly Thr Leu Val Lys Ala Thr Asp Thr Leu Ile
225                 230                 235                 240

Glu Asn Cys Ala Lys Glu Val Ile Ala Ile Val Thr His Gly Ile Phe
                245                 250                 255

Ser Gly Gly Ala Arg Glu Lys Leu Arg Asn Ser Lys Leu Ala Arg Ile
            260                 265                 270

Val Ser Thr Asn Thr Val Pro Val Asp Leu Asn Leu Asp Ile Tyr His
        275                 280                 285

Gln Ile Asp Ile Ser Ala Ile Leu Ala Glu Ala Ile Arg Arg Leu His
    290                 295                 300

Asn Gly Glu Ser Val Ser Tyr Leu Phe Asn Asn Ala Val Met
305                 310                 315

(2) INFORMATION FOR SEQ ID NO: 3:

(i) SEQUENCE CHARACTERISTICS:
        (A) LENGTH: 5369 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: 5'UTR
        (B) LOCATION: 1..54

(ix) FEATURE:
        (A) NAME/KEY: CDS
        (B) LOCATION: 55..1482

(ix) FEATURE:
        (A) NAME/KEY: CDS
        (B) LOCATION: 1767..3299

(ix) FEATURE:
        (A) NAME/KEY: CDS
        (B) LOCATION: 3588..4703

(ix) FEATURE:
        (A) NAME/KEY: 3'UTR
        (B) LOCATION: 4704..5369

(xi) SEQUENCE DESCRIPTION: SEQ ID NO: 3:

AAGCTTGACC TTGGCTGGCA CTTGAGTCGG CAGACAGGTG GACTAACCCG A GCA ATG         57
                                                        Met
                                                          1

GAT CGT GGT TGT AAA GGT ATC TCT TAT GTG CTC AGT GCA ATG GTT TTT         105
Asp Arg Gly Cys Lys Gly Ile Ser Tyr Val Leu Ser Ala Met Val Phe
            5                   10                  15

CAC ATA ATA CCG ATT ACA TTT GAA ATA TCG ATG GTA TGT GGC ATA TTG         153
His Ile Ile Pro Ile Thr Phe Glu Ile Ser Met Val Cys Gly Ile Leu
        20                  25                  30

ACA TAC CAG TTT GGT GCT TCC TTC GCT GCT ATA ACA TTC TCG ACT ATG         201
Thr Tyr Gln Phe Gly Ala Ser Phe Ala Ala Ile Thr Phe Ser Thr Met
    35                  40                  45
```

```
CTT CTT TAC TCC ATC TTT ACT TTC AGA ACG A CG GCG TGG CGC ACA CGG         249
Leu Leu Tyr Ser Ile Phe Thr Phe Arg Thr T hr Ala Trp Arg Thr Arg
 50                  55                  60                  65

TTT AGG CGT GAT GCG AAC AAG GCT GAC AAT A AG GCC GCT AGT GTG GCA         297
Phe Arg Arg Asp Ala Asn Lys Ala Asp Asn L ys Ala Ala Ser Val Ala
                 70                  75                  80

TTG GAT TCC CTA ATA AAT TTT GAA GCT GTA A AG TAT TTC AAT AAC GAG         345
Leu Asp Ser Leu Ile Asn Phe Glu Ala Val L ys Tyr Phe Asn Asn Glu
             85                  90                  95

AAG TAC CTT GCG GAC AAG TAT CAC ACA TCC T TG ATG AAG TAC CGG GAT         393
Lys Tyr Leu Ala Asp Lys Tyr His Thr Ser L eu Met Lys Tyr Arg Asp
         100                 105                 110

TCC CAG ATA AAG GTC TCG CAA TCG CTG GCG T TT TTG AAC ACC GGC CAG         441
Ser Gln Ile Lys Val Ser Gln Ser Leu Ala P he Leu Asn Thr Gly Gln
     115                 120                 125

AAC CTA ATT TTT ACC ACT GCA CTG ACT GCA A TG ATG TAT ATG GCC TGT         489
Asn Leu Ile Phe Thr Thr Ala Leu Thr Ala M et Met Tyr Met Ala Cys
130                 135                 140                 145

AAT GGT GTT ATG CAG GGC TCT CTT ACA GTG G GG GAT CTT GTG TTA ATT         537
Asn Gly Val Met Gln Gly Ser Leu Thr Val G ly Asp Leu Val Leu Ile
                150                 155                 160

AAT CAA CTG GTA TTC CAG CTC TCC GTG CCA C TA AAC TTC CTT GGT AGC         585
Asn Gln Leu Val Phe Gln Leu Ser Val Pro L eu Asn Phe Leu Gly Ser
            165                 170                 175

GTC TAC CGT GAT CTC AAG CAG TCT CTG ATA G AT ATG GAA TCT TTA TTT         633
Val Tyr Arg Asp Leu Lys Gln Ser Leu Ile A sp Met Glu Ser Leu Phe
        180                 185                 190

AAA CTG CAA AAA AAT CAG GTC ACA ATT AAG A AC TCC CCA AAT GCC CAG         681
Lys Leu Gln Lys Asn Gln Val Thr Ile Lys A sn Ser Pro Asn Ala Gln
    195                 200                 205

AAC CTA CCA ATA CAC AAA CCG TTG GAT ATT C GC TTT GAA AAT GTT ACG         729
Asn Leu Pro Ile His Lys Pro Leu Asp Ile A rg Phe Glu Asn Val Thr
210                 215                 220                 225

TTT GGC TAT GAC CCG GAG CGG CGT ATA TTG A AC AAT GTT TCG TTT ACC         777
Phe Gly Tyr Asp Pro Glu Arg Arg Ile Leu A sn Asn Val Ser Phe Thr
                230                 235                 240

ATC CCA GCT GGA ATG AAG ACT GCC ATA GTA G GC CCA TCG GGC TCG GGG         825
Ile Pro Ala Gly Met Lys Thr Ala Ile Val G ly Pro Ser Gly Ser Gly
            245                 250                 255

AAG TCC ACC ATT TTG AAG CTC GTA TTT AGA T TC TAT GAG CCC GAG CAA         873
Lys Ser Thr Ile Leu Lys Leu Val Phe Arg P he Tyr Glu Pro Glu Gln
        260                 265                 270

GGT CGT ATC CTA GTT GGC GGC ACA GAT ATC C GC GAT TTA GAC TTG CTT         921
Gly Arg Ile Leu Val Gly Gly Thr Asp Ile A rg Asp Leu Asp Leu Leu
    275                 280                 285

TCT TTA CGG AAG GCT ATC GGT GTC GTG CCC C AA GAT ACT CCT CTC TTC         969
Ser Leu Arg Lys Ala Ile Gly Val Val Pro G ln Asp Thr Pro Leu Phe
290                 295                 300                 305

AAT GAC ACA ATC TGG GAG AAT GTT AAA TTC G GC AAT ATC AGT TCC TCT        1017
Asn Asp Thr Ile Trp Glu Asn Val Lys Phe G ly Asn Ile Ser Ser Ser
                310                 315                 320

GAC GAT GAG ATT CTC AGG GCC ATA GAA AAA G CT CAA CTC ACG AAG CTA        1065
Asp Asp Glu Ile Leu Arg Ala Ile Glu Lys A la Gln Leu Thr Lys Leu
            325                 330                 335

CTC CAG AAC CTA CCA AAG GGC GCT TCC ACC G TT GTA GGG GAG CGC GGT        1113
Leu Gln Asn Leu Pro Lys Gly Ala Ser Thr V al Val Gly Glu Arg Gly
        340                 345                 350

TTG ATG ATC AGC GGA GGT GAG AAA CAA AGG C TT GCT ATT GCT CGT GTG        1161
Leu Met Ile Ser Gly Gly Glu Lys Gln Arg L eu Ala Ile Ala Arg Val
```

-continued

```
          355                 360                 365
CTT TTG AAG GAC GCT CCG CTG ATG TTT TTC G AC GAG GCT ACA AGT GCT    1209
Leu Leu Lys Asp Ala Pro Leu Met Phe Phe A sp Glu Ala Thr Ser Ala
370                 375                 380                 385

CTG GAT ACA CAC ACA GAG CAG GCA CTC TTG C AC ACC ATT CAG CAG AAC    1257
Leu Asp Thr His Thr Glu Gln Ala Leu Leu H is Thr Ile Gln Gln Asn
                390                 395                 400

TTT TCT TCC AAT TCA AAG ACG AGC GTT TAC G TT GCC CAT AGA CTG CGC    1305
Phe Ser Ser Asn Ser Lys Thr Ser Val Tyr V al Ala His Arg Leu Arg
            405                 410                 415

ACA ATC GCT GAT GCA GAT AAG ATC ATT GTT C TT GAA CAA GGT TCT GTC    1353
Thr Ile Ala Asp Ala Asp Lys Ile Ile Val L eu Glu Gln Gly Ser Val
            420                 425                 430

CGC GAA GAG GGC ACA CAC AGC TCG CTG TTA G CG TCA CAA GGA TCC CTA    1401
Arg Glu Glu Gly Thr His Ser Ser Leu Leu A la Ser Gln Gly Ser Leu
        435                 440                 445

TAC CGG GGT CTG TGG GAT ATT CAG GAA AAC C TA ACG CTT CCG GAA CGG    1449
Tyr Arg Gly Leu Trp Asp Ile Gln Glu Asn L eu Thr Leu Pro Glu Arg
450                 455                 460                 465

CCT GAG CAG TCA ACC GGA TCT CAG CAT GCA T AGACGTCTG ACTAGAGATT       1499
Pro Glu Gln Ser Thr Gly Ser Gln His Ala
                470                 475

ATATAATAAC CCTCGAGCCA AAATTATACG GCGCTAACAA GTAAAAATTT T AGTTACTTT  1559

TCTGACTTCT CTACGCTGAC TTCTCTACCC TTCTAACATA GTTAATTGAA G TAGTGGTTA  1619

ATGACGACTG CATTTTATTA TTGTCCACTT TGCATTAGAA GTACTAGTGC T TAAGCGCTC  1679

TTTAGGCCGC TTTCTTCTTC TTTGTCAGGC CGCAAGGTAA AGGAAGCACC A ACGGATTGC  1739

TACCGCTGCT ATTCCTGCTC TCTCAAG ATG TGT GGC ATA TTA GGC GTT GTG       1790
                            Met Cys Gly Il e Leu Gly Val Val
                             1                  5

CTA GCC GAT CAG TCG AAG GTG GTC GCC CCT G AG TTG TTT GAT GGC TCA    1838
Leu Ala Asp Gln Ser Lys Val Val Ala Pro G lu Leu Phe Asp Gly Ser
        10                  15                  20

CTG TTC TTA CAG CAT CGC GGT CAA GAT GCT G CC GGG ATT GCT ACG TGC    1886
Leu Phe Leu Gln His Arg Gly Gln Asp Ala A la Gly Ile Ala Thr Cys
25                  30                  35                  40

GGC CCC GGT GGG CGC TTG TAC CAA TGT AAG G GC AAT GGT ATG GCA CGG    1934
Gly Pro Gly Gly Arg Leu Tyr Gln Cys Lys G ly Asn Gly Met Ala Arg
                45                  50                  55

GAC GTG TTC ACG CAA GCT CGG ATG TCA GGG T TG GTT GGC TCT ATG GGG    1982
Asp Val Phe Thr Gln Ala Arg Met Ser Gly L eu Val Gly Ser Met Gly
                60                  65                  70

ATT GCA CAC CTG AGA TAT CCC ACT GCA GGC T CC AGT GCG AAC TCA GAA    2030
Ile Ala His Leu Arg Tyr Pro Thr Ala Gly S er Ser Ala Asn Ser Glu
            75                  80                  85

GCG CAG CCA TTC TAT GTG AAT AGT CCC TAC G GA ATT TGC ATG AGT CAT    2078
Ala Gln Pro Phe Tyr Val Asn Ser Pro Tyr G ly Ile Cys Met Ser His
        90                  95                  100

AAT GGT AAT CTG GTG AAC ACG ATG TCT CTA C GT AGA TAT CTT GAT GAA    2126
Asn Gly Asn Leu Val Asn Thr Met Ser Leu A rg Arg Tyr Leu Asp Glu
105                 110                 115                 120

GAC GTT CAC CGT CAT ATT AAC ACG GAC AGC G AT TCT GAG CTA CTG CTT    2174
Asp Val His Arg His Ile Asn Thr Asp Ser A sp Ser Glu Leu Leu Leu
                125                 130                 135

AAT ATA TTT GCC GCG GAG CTG GAA AAG TAC A AC AAA TAT CGT GTG AAC    2222
Asn Ile Phe Ala Ala Glu Leu Glu Lys Tyr A sn Lys Tyr Arg Val Asn
                140                 145                 150

AAC GAT GAT ATA TTT TGT GCT CTA GAG GGT G TT TAC AAA CGT TGT CGC    2270
```

-continued

```
Asn Asp Asp Ile Phe Cys Ala Leu Glu Gly V al Tyr Lys Arg Cys Arg
            155                 160                 165

GGT GGC TAT GCT TGT GTT GGC ATG TTG GCG G GA TAT GGA TTG TTT GGT    2318
Gly Gly Tyr Ala Cys Val Gly Met Leu Ala G ly Tyr Gly Leu Phe Gly
170                 175                 180

TTC CGG GAC CCC AAT GGG ATC AGG CCG CTA T TG TTT GGT GAG CGC GTC    2366
Phe Arg Asp Pro Asn Gly Ile Arg Pro Leu L eu Phe Gly Glu Arg Val
185                 190                 195                 200

AAC GAT GAC GGC ACC ATG GAC TAC ATG CTA G CG TCC GAA AGT GTC GTT    2414
Asn Asp Asp Gly Thr Met Asp Tyr Met Leu A la Ser Glu Ser Val Val
            205                 210                 215

CTT AAG GCC CAC CGC TTC CAA AAC ATA CGT G AT ATT CTT CCC GGC CAA    2462
Leu Lys Ala His Arg Phe Gln Asn Ile Arg A sp Ile Leu Pro Gly Gln
            220                 225                 230

GCC GTC ATT ATC CCT AAA ACG TGC GGC TCC A GT CCA CCA GAG TTC CGG    2510
Ala Val Ile Ile Pro Lys Thr Cys Gly Ser S er Pro Pro Glu Phe Arg
            235                 240                 245

CAG GTA GTG CCA ATT GAG GCC TAC AAA CCG G AC TTG TTT GAG TAC GTG    2558
Gln Val Val Pro Ile Glu Ala Tyr Lys Pro A sp Leu Phe Glu Tyr Val
            250                 255                 260

TAT TTC GCT CGT GCT GAC AGC GTT CTG GAC G GT ATT TCC GTT TAC CAT    2606
Tyr Phe Ala Arg Ala Asp Ser Val Leu Asp G ly Ile Ser Val Tyr His
265                 270                 275                 280

ACA CGC CTG TTG ATG GGT ATC AAA CTT GCC G AG AAC ATC AAA AAA CAG    2654
Thr Arg Leu Leu Met Gly Ile Lys Leu Ala G lu Asn Ile Lys Lys Gln
            285                 290                 295

ATC GAT CTG GAC GAA ATT GAC GTT GTT GTA T CT GTT CCT GAC ACT GCA    2702
Ile Asp Leu Asp Glu Ile Asp Val Val Val S er Val Pro Asp Thr Ala
            300                 305                 310

CGT ACC TGT GCA TTG GAG TGT GCC AAC CAT T TA AAC AAA CCT TAT CGC    2750
Arg Thr Cys Ala Leu Glu Cys Ala Asn His L eu Asn Lys Pro Tyr Arg
            315                 320                 325

GAA GGA TTT GTC AAG AAC AGA TAT GTT GGA A GA ACA TTT ATC ATG CCA    2798
Glu Gly Phe Val Lys Asn Arg Tyr Val Gly A rg Thr Phe Ile Met Pro
            330                 335                 340

AAC CAA AAA GAG CGA GTA TCT TCT GTG CGC C GC AAG TTG AAC CCA ATG    2846
Asn Gln Lys Glu Arg Val Ser Ser Val Arg A rg Lys Leu Asn Pro Met
345                 350                 355                 360

AAC TCA GAA TTT AAA GAC AAG CGC GTG CTG A TT GTC GAT GAT TCC ATT    2894
Asn Ser Glu Phe Lys Asp Lys Arg Val Leu I le Val Asp Asp Ser Ile
            365                 370                 375

GTG CGA GGT ACC ACT TCC AAA GAG ATT GTT A AC ATG GCG AAG GAA TCC    2942
Val Arg Gly Thr Thr Ser Lys Glu Ile Val A sn Met Ala Lys Glu Ser
            380                 385                 390

GGT GCT GCC AAG GTC TAC TTT GCC TCT GCA G CG CCA GCA ATT CGT TTC    2990
Gly Ala Ala Lys Val Tyr Phe Ala Ser Ala A la Pro Ala Ile Arg Phe
            395                 400                 405

AAT CAC ATC TAC GGG ATT GAC CTA GCA GAT A CT AAG CAG CTT GTC GCC    3038
Asn His Ile Tyr Gly Ile Asp Leu Ala Asp T hr Lys Gln Leu Val Ala
            410                 415                 420

TAC AAC AGA ACT GTT GAA GAA ATC ACT GCG G AG CTG GGC TGT GAC CGC    3086
Tyr Asn Arg Thr Val Glu Glu Ile Thr Ala G lu Leu Gly Cys Asp Arg
425                 430                 435                 440

GTC ATC TAT CAA TCT TTG GAT GAC CTC ATC G AC TGT TGC AAG ACA GAC    3134
Val Ile Tyr Gln Ser Leu Asp Asp Leu Ile A sp Cys Cys Lys Thr Asp
            445                 450                 455

ATC ATC TCA GAA TTT GAA GTT GGA GTT TTC A CT GGT AAC TAC GTT ACA    3182
Ile Ile Ser Glu Phe Glu Val Gly Val Phe T hr Gly Asn Tyr Val Thr
            460                 465                 470
```

```
GGT GTT GAG GAT GTG TAC TTG CAG GAA TTA G AA CGT TGC CGC GCT CTT      3230
Gly Val Glu Asp Val Tyr Leu Gln Glu Leu G lu Arg Cys Arg Ala Leu
            475                 480                 485

AAT AAC TCG AAT AAG GGT GAA GCG AAG GCC G AG GTT GAT ATT GGT CTC      3278
Asn Asn Ser Asn Lys Gly Glu Ala Lys Ala G lu Val Asp Ile Gly Leu
            490                 495                 500

TAC AAT TCT GCC GAC TAT TAGCGGCGCC GTTGCCGGCA T CCGGCCCCA             3326
Tyr Asn Ser Ala Asp Tyr
505             510

TATATAGACT CATCGGGACC TAAAATAAGC CTTTACAGAT CATTATCTAC A AATATAGAT    3386

ACCATTAAAA GCCTGACTTT CGACTTACTC CTAGCACACC CCGTTGTATC C CTGTGCTTG   3446

CTTTCTTAAA TGCCGTTGGT TAGGCTTTGG ACTTAGCGTC CCGCCCATTT T CTAGCATGT   3506

GCAGATCTAG CAAATTTGGC CTAAGACAAG AAGATCCATT CGGCACCCAC A TCCTGGAGC   3566

CAGCACACAG TGGACCCAGA C ATG AGC AGC GGC AAT ATA  TGG AAG CAA TTG     3617
                        Met Ser Ser Gly Asn Ile  Trp Lys Gln Leu
                         1               5                   10

CTA GAG GAG AAT AGC GAA CAG CTG GAC CAG T CC ACT ACG GAG ACT TAC      3665
Leu Glu Glu Asn Ser Glu Gln Leu Asp Gln S er Thr Thr Glu Thr Tyr
            15                  20                  25

GTG GTA TGC TGC GAG AAC GAA GAT TCC CTT A AC CAG TTT TTG CAA CAA      3713
Val Val Cys Cys Glu Asn Glu Asp Ser Leu A sn Gln Phe Leu Gln Gln
            30                  35                  40

TGT TGG CAG ATT GAC GAG GGC GAG AAG GTG A CC AAC CTG GAG CCG TTG      3761
Cys Trp Gln Ile Asp Glu Gly Glu Lys Val T hr Asn Leu Glu Pro Leu
            45                  50                  55

GGA TTC TTT ACA AAG GTG GTT TCG CGC GAC G AA GAG AAC CTC CGG CTC      3809
Gly Phe Phe Thr Lys Val Val Ser Arg Asp G lu Glu Asn Leu Arg Leu
            60                  65                  70

AAC GTA TAC TAT GCC AAG AGC CCA CTG GAT G CA CAG ACG CTG CAG TTT      3857
Asn Val Tyr Tyr Ala Lys Ser Pro Leu Asp A la Gln Thr Leu Gln Phe
75                  80                  85                  90

CTG GGC GTG TTC CTG CGC CAA ATG GAA ACC T CA CAA ATA CGT TGG ATC      3905
Leu Gly Val Phe Leu Arg Gln Met Glu Thr S er Gln Ile Arg Trp Ile
            95                  100                 105

TTC CTA CTG GAC TGG CTG CTA GAC GAT AAA C GA TTA TGG CTA CGT CAA      3953
Phe Leu Leu Asp Trp Leu Leu Asp Asp Lys A rg Leu Trp Leu Arg Gln
            110                 115                 120

CTG CGG AAC TCG TGG GCC GCC TTG GAG GAA G CG CAG GTG GCA CCC TTT      4001
Leu Arg Asn Ser Trp Ala Ala Leu Glu Glu A la Gln Val Ala Pro Phe
            125                 130                 135

CCA GGT GGC GCT GTG GTG GTG GTC CTC AAC C CG AGT CAC GTG ACA CAA      4049
Pro Gly Gly Ala Val Val Val Val Leu Asn P ro Ser His Val Thr Gln
            140                 145                 150

CTG GAG CGA AAC ACG ATG GTT TGG AAC TCC C GC CGT CTG GAC CTG GTA      4097
Leu Glu Arg Asn Thr Met Val Trp Asn Ser A rg Arg Leu Asp Leu Val
155                 160                 165                 170

CAC CAG ACA CTG CGA GCT GCA TGC CTC AAC A CC GGC TCG GCG CTA GTT      4145
His Gln Thr Leu Arg Ala Ala Cys Leu Asn T hr Gly Ser Ala Leu Val
            175                 180                 185

ACA CTT GAT CCT AAT ACT GCG CGC GAA GAC G TC ATG CAC ATA TGT GCG      4193
Thr Leu Asp Pro Asn Thr Ala Arg Glu Asp V al Met His Ile Cys Ala
            190                 195                 200

CTG CTT GCG GGG CTG CCT ACA TCC CGT CCC G TC GCG ATG CTA AGC CTG      4241
Leu Leu Ala Gly Leu Pro Thr Ser Arg Pro V al Ala Met Leu Ser Leu
            205                 210                 215

CAA AGT CTA TTC ATC CCC CAC GGT GCA GAT T CC ATC GGC AAG ATC TGC      4289
Gln Ser Leu Phe Ile Pro His Gly Ala Asp S er Ile Gly Lys Ile Cys
            220                 225                 230
```

```
ACC ATC GCG CCC GAG TTC CCT GTT GCT ACG G TG TTC GAC AAC GAT TTT      4337
Thr Ile Ala Pro Glu Phe Pro Val Ala Thr V al Phe Asp Asn Asp Phe
235                 240                 245                 250

GTG AGC TCG ACA TTC GAG GCC GCA ATT GCT C CA GAA CTT ACT CCA GGA      4385
Val Ser Ser Thr Phe Glu Ala Ala Ile Ala P ro Glu Leu Thr Pro Gly
                255                 260                 265

CCA CGT GTG CCA TCT GAC CAC CCA TGG CTA A CA GAG CCT ACC AAC CCC      4433
Pro Arg Val Pro Ser Asp His Pro Trp Leu T hr Glu Pro Thr Asn Pro
            270                 275                 280

CCT TCG GAG GCA ACC GCT TGG CAT TTC GAT C TC CAA GGT CGC CTC GCT      4481
Pro Ser Glu Ala Thr Ala Trp His Phe Asp L eu Gln Gly Arg Leu Ala
            285                 290                 295

ACC CTA TAC CGG CAT CTT GGT GAC TCT AAC A AG GCC ATA TCT GTT ACT      4529
Thr Leu Tyr Arg His Leu Gly Asp Ser Asn L ys Ala Ile Ser Val Thr
        300                 305                 310

CAG CAC CGC TTC CAC AAG CCC CGC TCG GAA G AT TAT GCA TAC GAA TTC      4577
Gln His Arg Phe His Lys Pro Arg Ser Glu A sp Tyr Ala Tyr Glu Phe
315                 320                 325                 330

GAG CTG CCG TCT AAG CAC CCT ACA ATA CGT G AC CTC ATA CGC TCT GCC      4625
Glu Leu Pro Ser Lys His Pro Thr Ile Arg A sp Leu Ile Arg Ser Ala
            335                 340                 345

GCA GCC GAC TCA CCG AAC GAC GTC GCT GAC T CC ATC GAT GGG CTT ATG      4673
Ala Ala Asp Ser Pro Asn Asp Val Ala Asp S er Ile Asp Gly Leu Met
            350                 355                 360

GAT GGT ATC GTA CAA AGG AAT GTT CAT TGACGTCG AC ACAAAAATTT           4720
Asp Gly Ile Val Gln Arg Asn Val His
            365                 370

TGTTACTGTT CTCTCGAGAA CTATTCTCAT CCAGTACTGA CATATTAGAA G GCGAAGTGA   4780

ACTAGGATTT ATATAAAGTA GCCTTCAGGC AATTGCACAG GGTCTATTGA G TCGCTGCCG   4840

TTCACGAGAG AGCCCAATAT ATCGAGGACT AATTGGTCAC TTTTGTTTTG C TATACTCAC   4900

CCTGTATTTG CTAATCATTT ATCCGCTTTG TCCAAGTGGT TGCGAAGATA T CGAGCCAGA   4960

ACATTAGAAT CTGGTTTGCC GCATCCTAGA GCTGTCTCCA AGCCAGTTGA A CCGTTGCGG   5020

GAGATTACCG CAGCCGGTTT GATCAGAGTA CTGGTGACTG CCAGCACCCA C GTTTGTGAC   5080

TTATAAATAT ACGCCCTGTG GAGCCATAGC CATTGGCATA AAGAGAAGAG C ACCCCGTGC   5140

CACGATGCAG ACACTTCCGG TGTACCCAGC GTCACAGACT GCGTCGCCTA C GAAGCGTGA   5200

ACTTGCAGCG GCGCCCTCGG TGCCGCAGGA CGGCGCCCGG CTGCCTGCGC A GCTCACTTT   5260

AGTGACGCCC CCAGAACCTG ATATCCAGAA GAAGTCAGTG CGATCTCAGG T CGCGCGTTT   5320

AAGCATCTCG GAGACAGATG TAGTGAAGAG TGATATCGTG GCTAAGCTT              5369

(2) INFORMATION FOR SEQ ID NO: 4:

(i) SEQUENCE CHARACTERISTICS:
        (A) LENGTH: 475 amino acids
        (B) TYPE: amino acid
        (D) TOPOLOGY: linear (ii) MOLECULE TYPE: protein (xi) SEQUENCE DESCRIPTION: SEQ ID NO: 4:

Met Asp Arg Gly Cys Lys Gly Ile Ser Tyr V al Leu Ser Ala Met Val
1               5                   10                  15

Phe His Ile Ile Pro Ile Thr Phe Glu Ile S er Met Val Cys Gly Ile
            20                  25                  30

Leu Thr Tyr Gln Phe Gly Ala Ser Phe Ala A la Ile Thr Phe Ser Thr
        35                  40                  45
```

```
Met Leu Leu Tyr Ser Ile Phe Thr Phe Arg Thr Thr Ala Trp Arg Thr
 50                  55                  60
Arg Phe Arg Arg Asp Ala Asn Lys Ala Asp Asn Lys Ala Ala Ser Val
 65                  70                  75                  80
Ala Leu Asp Ser Leu Ile Asn Phe Glu Ala Val Lys Tyr Phe Asn Asn
                 85                  90                  95
Glu Lys Tyr Leu Ala Asp Lys Tyr His Thr Ser Leu Met Lys Tyr Arg
                100                 105                 110
Asp Ser Gln Ile Lys Val Ser Gln Ser Leu Ala Phe Leu Asn Thr Gly
            115                 120                 125
Gln Asn Leu Ile Phe Thr Thr Ala Leu Thr Ala Met Met Tyr Met Ala
        130                 135                 140
Cys Asn Gly Val Met Gln Gly Ser Leu Thr Val Gly Asp Leu Val Leu
145                 150                 155                 160
Ile Asn Gln Leu Val Phe Gln Leu Ser Val Pro Leu Asn Phe Leu Gly
                165                 170                 175
Ser Val Tyr Arg Asp Leu Lys Gln Ser Leu Ile Asp Met Glu Ser Leu
            180                 185                 190
Phe Lys Leu Gln Lys Asn Gln Val Thr Ile Lys Asn Ser Pro Asn Ala
        195                 200                 205
Gln Asn Leu Pro Ile His Lys Pro Leu Asp Ile Arg Phe Glu Asn Val
    210                 215                 220
Thr Phe Gly Tyr Asp Pro Glu Arg Arg Ile Leu Asn Asn Val Ser Phe
225                 230                 235                 240
Thr Ile Pro Ala Gly Met Lys Thr Ala Ile Val Gly Pro Ser Gly Ser
                245                 250                 255
Gly Lys Ser Thr Ile Leu Lys Leu Val Phe Arg Phe Tyr Glu Pro Glu
            260                 265                 270
Gln Gly Arg Ile Leu Val Gly Gly Thr Asp Ile Arg Asp Leu Asp Leu
        275                 280                 285
Leu Ser Leu Arg Lys Ala Ile Gly Val Val Pro Gln Asp Thr Pro Leu
    290                 295                 300
Phe Asn Asp Thr Ile Trp Glu Asn Val Lys Phe Gly Asn Ile Ser Ser
305                 310                 315                 320
Ser Asp Asp Glu Ile Leu Arg Ala Ile Glu Lys Ala Gln Leu Thr Lys
                325                 330                 335
Leu Leu Gln Asn Leu Pro Lys Gly Ala Ser Thr Val Val Gly Glu Arg
            340                 345                 350
Gly Leu Met Ile Ser Gly Gly Glu Lys Gln Arg Leu Ala Ile Ala Arg
        355                 360                 365
Val Leu Leu Lys Asp Ala Pro Leu Met Phe Phe Asp Glu Ala Thr Ser
    370                 375                 380
Ala Leu Asp Thr His Thr Glu Gln Ala Leu Leu His Thr Ile Gln Gln
385                 390                 395                 400
Asn Phe Ser Ser Asn Ser Lys Thr Ser Val Tyr Val Ala His Arg Leu
                405                 410                 415
Arg Thr Ile Ala Asp Ala Asp Lys Ile Ile Val Leu Glu Gln Gly Ser
            420                 425                 430
Val Arg Glu Glu Gly Thr His Ser Ser Leu Leu Ala Ser Gln Gly Ser
        435                 440                 445
Leu Tyr Arg Gly Leu Trp Asp Ile Gln Glu Asn Leu Thr Leu Pro Glu
    450                 455                 460
```

```
Arg Pro Glu Gln Ser Thr Gly Ser Gln His Ala
465                 470                 475

(2) INFORMATION FOR SEQ ID NO: 5:

(i) SEQUENCE CHARACTERISTICS:
        (A) LENGTH: 510 amino acids
        (B) TYPE: amino acid
        (D) TOPOLOGY: linear (ii) MOLECULE TYPE: protein (xi) SEQUENCE DESCRIPTION: SEQ ID NO: 5:

Met Cys Gly Ile Leu Gly Val Val Leu Ala Asp Gln Ser Lys Val Val
1               5                   10                  15

Ala Pro Glu Leu Phe Asp Gly Ser Leu Phe Leu Gln His Arg Gly Gln
                20                  25                  30

Asp Ala Ala Gly Ile Ala Thr Cys Gly Pro Gly Gly Arg Leu Tyr Gln
            35                  40                  45

Cys Lys Gly Asn Gly Met Ala Arg Asp Val Phe Thr Gln Ala Arg Met
        50                  55                  60

Ser Gly Leu Val Gly Ser Met Gly Ile Ala His Leu Arg Tyr Pro Thr
65                  70                  75                  80

Ala Gly Ser Ser Ala Asn Ser Glu Ala Gln Pro Phe Tyr Val Asn Ser
                85                  90                  95

Pro Tyr Gly Ile Cys Met Ser His Asn Gly Asn Leu Val Asn Thr Met
                100                 105                 110

Ser Leu Arg Arg Tyr Leu Asp Glu Asp Val His Arg His Ile Asn Thr
                115                 120                 125

Asp Ser Asp Ser Glu Leu Leu Leu Asn Ile Phe Ala Ala Glu Leu Glu
            130                 135                 140

Lys Tyr Asn Lys Tyr Arg Val Asn Asn Asp Ile Phe Cys Ala Leu
145                 150                 155                 160

Glu Gly Val Tyr Lys Arg Cys Arg Gly Gly Tyr Ala Cys Val Gly Met
                165                 170                 175

Leu Ala Gly Tyr Gly Leu Phe Gly Phe Arg Asp Pro Asn Gly Ile Arg
            180                 185                 190

Pro Leu Leu Phe Gly Glu Arg Val Asn Asp Asp Gly Thr Met Asp Tyr
            195                 200                 205

Met Leu Ala Ser Glu Ser Val Val Leu Lys Ala His Arg Phe Gln Asn
            210                 215                 220

Ile Arg Asp Ile Leu Pro Gly Gln Ala Val Ile Ile Pro Lys Thr Cys
225                 230                 235                 240

Gly Ser Ser Pro Pro Glu Phe Arg Gln Val Val Pro Ile Glu Ala Tyr
                245                 250                 255

Lys Pro Asp Leu Phe Glu Tyr Val Tyr Phe Ala Arg Ala Asp Ser Val
            260                 265                 270

Leu Asp Gly Ile Ser Val Tyr His Thr Arg Leu Leu Met Gly Ile Lys
            275                 280                 285

Leu Ala Glu Asn Ile Lys Lys Gln Ile Asp Leu Asp Glu Ile Asp Val
            290                 295                 300

Val Val Ser Val Pro Asp Thr Ala Arg Thr Cys Ala Leu Glu Cys Ala
305                 310                 315                 320

Asn His Leu Asn Lys Pro Tyr Arg Glu Gly Phe Val Lys Asn Arg Tyr
                325                 330                 335

Val Gly Arg Thr Phe Ile Met Pro Asn Gln Lys Glu Arg Val Ser Ser
```

```
                  340             345             350
Val Arg Arg Lys Leu Asn Pro Met Asn Ser G lu Phe Lys Asp Lys Arg
                355             360              365
Val Leu Ile Val Asp Asp Ser Ile Val Arg G ly Thr Thr Ser Lys Glu
    370             375              380
Ile Val Asn Met Ala Lys Glu Ser Gly Ala A la Lys Val Tyr Phe Ala
385             390              395                         400
Ser Ala Ala Pro Ala Ile Arg Phe Asn His I le Tyr Gly Ile Asp Leu
                405             410              415
Ala Asp Thr Lys Gln Leu Val Ala Tyr Asn A rg Thr Val Glu Glu Ile
                420             425              430
Thr Ala Glu Leu Gly Cys Asp Arg Val Ile T yr Gln Ser Leu Asp Asp
                435             440              445
Leu Ile Asp Cys Cys Lys Thr Asp Ile Ile S er Glu Phe Glu Val Gly
    450             455              460
Val Phe Thr Gly Asn Tyr Val Thr Gly Val G lu Asp Val Tyr Leu Gln
465             470             475                          480
Glu Leu Glu Arg Cys Arg Ala Leu Asn Asn S er Asn Lys Gly Glu Ala
                485             490              495
Lys Ala Glu Val Asp Ile Gly Leu Tyr Asn S er Ala Asp Tyr
                500             505              510

(2) INFORMATION FOR SEQ ID NO: 6:

(i) SEQUENCE CHARACTERISTICS:
        (A) LENGTH: 371 amino acids
        (B) TYPE: amino acid
        (D) TOPOLOGY: linear (ii) MOLECULE TYPE: protein (xi) SEQUENCE DESCRIPTION: SEQ ID NO: 6:

Met Ser Ser Gly Asn Ile Trp Lys Gln Leu L eu Glu Glu Asn Ser Glu
 1               5              10               15
Gln Leu Asp Gln Ser Thr Thr Glu Thr Tyr V al Val Cys Cys Glu Asn
                20              25               30
Glu Asp Ser Leu Asn Gln Phe Leu Gln Gln C ys Trp Gln Ile Asp Glu
        35              40                       45
Gly Glu Lys Val Thr Asn Leu Glu Pro Leu G ly Phe Phe Thr Lys Val
    50              55                       60
Val Ser Arg Asp Glu Glu Asn Leu Arg Leu A sn Val Tyr Tyr Ala Lys
65              70              75                           80
Ser Pro Leu Asp Ala Gln Thr Leu Gln Phe L eu Gly Val Phe Leu Arg
                85              90               95
Gln Met Glu Thr Ser Gln Ile Arg Trp Ile P he Leu Leu Asp Trp Leu
                100             105              110
Leu Asp Asp Lys Arg Leu Trp Leu Arg Gln L eu Arg Asn Ser Trp Ala
                115             120              125
Ala Leu Glu Glu Ala Gln Val Ala Pro Phe P ro Gly Gly Ala Val Val
                130             135              140
Val Val Leu Asn Pro Ser His Val Thr Gln L eu Glu Arg Asn Thr Met
145             150             155                          160
Val Trp Asn Ser Arg Arg Leu Asp Leu Val H is Gln Thr Leu Arg Ala
                165             170              175
Ala Cys Leu Asn Thr Gly Ser Ala Leu Val T hr Leu Asp Pro Asn Thr
                180             185              190
```

```
Ala Arg Glu Asp Val Met His Ile Cys Ala L eu Leu Ala Gly Leu Pro
        195                 200                 205

Thr Ser Arg Pro Val Ala Met Leu Ser Leu G ln Ser Leu Phe Ile Pro
        210                 215                 220

His Gly Ala Asp Ser Ile Gly Lys Ile Cys T hr Ile Ala Pro Glu Phe
225                 230                 235                 240

Pro Val Ala Thr Val Phe Asp Asn Asp Phe V al Ser Ser Thr Phe Glu
            245                 250                 255

Ala Ala Ile Ala Pro Glu Leu Thr Pro Gly P ro Arg Val Pro Ser Asp
            260                 265                 270

His Pro Trp Leu Thr Glu Pro Thr Asn Pro P ro Ser Glu Ala Thr Ala
        275                 280                 285

Trp His Phe Asp Leu Gln Gly Arg Leu Ala T hr Leu Tyr Arg His Leu
        290                 295                 300

Gly Asp Ser Asn Lys Ala Ile Ser Val Thr G ln His Arg Phe His Lys
305                 310                 315                 320

Pro Arg Ser Glu Asp Tyr Ala Tyr Glu Phe G lu Leu Pro Ser Lys His
            325                 330                 335

Pro Thr Ile Arg Asp Leu Ile Arg Ser Ala A la Ala Asp Ser Pro Asn
            340                 345                 350

Asp Val Ala Asp Ser Ile Asp Gly Leu Met A sp Gly Ile Val Gln Arg
            355                 360                 365

Asn Val His
    370

(2) INFORMATION FOR SEQ ID NO: 7:

(i) SEQUENCE CHARACTERISTICS:
        (A) LENGTH: 3616 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: 5'UTR
        (B) LOCATION: 1..863

(ix) FEATURE:
        (A) NAME/KEY: CDS
        (B) LOCATION: 864..1316

(ix) FEATURE:
        (A) NAME/KEY: intron
        (B) LOCATION: 1317..1477

(ix) FEATURE:
        (A) NAME/KEY: CDS
        (B) LOCATION: 1478..2592

(ix) FEATURE:
        (A) NAME/KEY: 3'UTR
        (B) LOCATION: 2593..3616

(xi) SEQUENCE DESCRIPTION: SEQ ID NO: 7:

GGGCCCGGTG CCAGCTCGCC AGGTGCGGAC TCGCGCTCGG GCTGTGGGCG C TCTACCTGC    60

TGCTGCTCGG CAGCTGCCTG ACGCGCGCGT ACGAGCTGTC GGATCTCGAA A ACCTGGAAT   120

CCGATTACTA CAGCTACGTG CTGGATGTGA ACTTCGCGCT GCTGAGCGCC A TGAGCGCGA   180
```

```
CCGGCCTCGC GATGGGCGCC GTGAGCGGCT CCCTCGGGAG CGCGCCGGTG C TCGCGCAGT      240

GGCCGGCAGC GATCTGGGCC GTGCGCTTCC TGCGCGCCGC GGGCTATGTC G CGATAGTCC      300

TAATCCTGCC GTTCCTGTCC GTCGTCGCAT TCCTGCAGCC GCTCTGCGAG C GCGCGCTGG      360

CGCTGTTCCC GTTTGTGCGC GCGTGGGGCA TGGACGGCGT GTTCAACTTC C TGCTGCTCT      420

CCGCCGTGCT CTGGACTGTA TTCCTGGCCG TTCGCCTGCT CCGCGCCGTC T ACAGACTGC      480

TGCGCTGGCT GGTCGGTCTT TTGGTCCGCC TGGCACGCCT GCTGCTGCGA G GCGCCCGTC      540

GGACGCCTGC GGCGGCCCCC GAGGAGCCCG TCTAGCGTGC GCGCGTTCTA G GCCCCTGAC      600

AGCTCCTACC TGGTGCTGGC CGCCGGTAGG GCTCGCATCG TGCGGCGCAG G CCCATTGCT      660

TTTTGGCCCC CGCTGGATCA TCGTTTCTTT TACGTGAAAA GTTTGCAGCG A TGAGCTGCA      720

GTATAAATAG GTTTTCTAGA TGCGCCAAAT CCCAGCTGGG TTTACCGGCG T CTGTTCGGG      780

ATAGTTACTT GATGGATGGG TCAACTTGAG AGCTTGGGTT TAGTGTTGAC T CCTTCTCTT      840

CATAGCACGC CGAACAAAGC GCA ATG ACT TAC AGA GAC G CA GCC ACG GCA          890
                         Met Thr Tyr Arg Asp Ala Ala Thr Ala
                          1              5

CTG GAG CAC CTG GCG ACG TAC GCC GAG AAG G AC GGG CTG TCC GTG GAG        938
Leu Glu His Leu Ala Thr Tyr Ala Glu Lys A sp Gly Leu Ser Val Glu
 10              15              20              25

CAG TTG ATG GAC TCC AAG ACG CGG GGC GGG T TG ACG TAC AAC GAC TTC        986
Gln Leu Met Asp Ser Lys Thr Arg Gly Gly L eu Thr Tyr Asn Asp Phe
         30              35              40

CTG GTC TTG CCG GGC AAG ATC GAC TTC CCA T CG TCG GAG GTG GTG CTG       1034
Leu Val Leu Pro Gly Lys Ile Asp Phe Pro S er Ser Glu Val Val Leu
             45              50              55

TCG TCG CGC CTG ACC AAG AAG ATC ACC TTG A AC GCG CCG TTT GTG TCG       1082
Ser Ser Arg Leu Thr Lys Lys Ile Thr Leu A sn Ala Pro Phe Val Ser
         60              65              70

TCG CCG ATG GAC ACG GTG ACG GAG GCC GAC A TG GCG ATC CAC ATG GCG       1130
Ser Pro Met Asp Thr Val Thr Glu Ala Asp M et Ala Ile His Met Ala
     75              80              85

CTC CTG GGC GGC ATC GGG ATC ATC CAC CAC A AC TGC ACT GCG GAG GAG       1178
Leu Leu Gly Gly Ile Gly Ile Ile His His A sn Cys Thr Ala Glu Glu
 90              95             100             105

CAG GCG GAG ATG GTG CGC CGG GTC AAG AAG T AC GAA AAC GGG TTC ATC       1226
Gln Ala Glu Met Val Arg Arg Val Lys Lys T yr Glu Asn Gly Phe Ile
         110             115             120

AAC GCC CCC GTG GTC GTG GGG CCG GAC GCG A CG GTG GCG GAC GTG CGC       1274
Asn Ala Pro Val Val Val Gly Pro Asp Ala T hr Val Ala Asp Val Arg
     125             130             135

CGG ATG AAG AAC GAG TTT GGG TTT GCA GGA T TT CCT GTG ACA               1316
Arg Met Lys Asn Glu Phe Gly Phe Ala Gly P he Pro Val Thr
 140             145             150

GGTATGTTAG AGTGGCACGC GGGGCTGCAC GCTGGGATGA TGATCATAAA T CAATAACTT     1376

TCGTTCTACT GACTGCGATC AAACGATCGT GTAGACACCT TTTACTCTGA C CGCAGACGT     1436

GCAGCGCCTT TTTGGCAGGA ACATGTACTA ACACATCAGC A GAT GAT  GGC AAG         1489
                                              Asp Asp  Gly Lys
                                                   1

CCG ACC GGG AAG CTG CAG GGG ATC ATC ACG T CC CGT GAC ATC CAG TTT       1537
Pro Thr Gly Lys Leu Gln Gly Ile Ile Thr S er Arg Asp Ile Gln Phe
  5              10              15              20

GTC GAG GAC GAG ACC CTG CTT GTG TCT GAG A TC ATG ACC AAG GAC GTC       1585
Val Glu Asp Glu Thr Leu Leu Val Ser Glu I le Met Thr Lys Asp Val
         25              30              35
```

```
ATC ACT GGG AAG CAG GGC ATC AAC CTC GAG G AG GCG AAC CAG ATC CTG      1633
Ile Thr Gly Lys Gln Gly Ile Asn Leu Glu G lu Ala Asn Gln Ile Leu
            40                  45                  50

AAG AAC ACC AAG AAG GGC AAG CTG CCA ATT G TG GAC GAG GCG GGC TGC      1681
Lys Asn Thr Lys Lys Gly Lys Leu Pro Ile V al Asp Glu Ala Gly Cys
            55                  60                  65

CTG GTG TCC ATG CTT TCG AGA ACT GAC TTG A TG AAG AAC CAG TCC TAC      1729
Leu Val Ser Met Leu Ser Arg Thr Asp Leu M et Lys Asn Gln Ser Tyr
        70                  75                  80

CCA TTG GCC TCC AAG TCT GCC GAC ACC AAG C AG CTG CTC TGT GGT GCT      1777
Pro Leu Ala Ser Lys Ser Ala Asp Thr Lys G ln Leu Leu Cys Gly Ala
 85             90                  95                 100

GCG ATC GGC ACC ATC GAC GCG GAC AGG CAG A GA CTG GCG ATG CTG TCG      1825
Ala Ile Gly Thr Ile Asp Ala Asp Arg Gln A rg Leu Ala Met Leu Val
                105                 110                 115

GAG GCC GGT CTG GAC GTT GTT GTG CTA GAC T CC TCG CAG GGT AAC TCG      1873
Glu Ala Gly Leu Asp Val Val Val Leu Asp S er Ser Gln Gly Asn Ser
                120                 125                 130

GTC TTC CAG ATC AAC ATG ATC AAG TGG ATC A AG GAG ACC TTC CCA GAC      1921
Val Phe Gln Ile Asn Met Ile Lys Trp Ile L ys Glu Thr Phe Pro Asp
            135                 140                 145

CTG CAG GTC ATT GCT GGC AAC GTG GTC ACC A GA GAG CAG GCT GCC AGC      1969
Leu Gln Val Ile Ala Gly Asn Val Val Thr A rg Glu Gln Ala Ala Ser
        150                 155                 160

TTG ATC CAC GCC GGC GCA GAC GGG TTG CGT A TC GGT ATG GGC TCT GGC      2017
Leu Ile His Ala Gly Ala Asp Gly Leu Arg I le Gly Met Gly Ser Gly
165                 170                 175                 180

TCC ATC TGT ATC ACT CAG GAG GTG ATG GCC T GT GGT AGA CCA CAG GGT      2065
Ser Ile Cys Ile Thr Gln Glu Val Met Ala C ys Gly Arg Pro Gln Gly
                185                 190                 195

ACC GCT GTC TAC AAC GTC ACG CAG TTC GCC A AC CAG TTT GGT GTG CCA      2113
Thr Ala Val Tyr Asn Val Thr Gln Phe Ala A sn Gln Phe Gly Val Pro
            200                 205                 210

TGT ATT GCT GAC GGT GGT GTC CAG AAC ATC G GG CAC ATT ACC AAA GCT      2161
Cys Ile Ala Asp Gly Gly Val Gln Asn Ile G ly His Ile Thr Lys Ala
            215                 220                 225

ATC GCT CTT GGC GCG TCC ACC GTC ATG ATG G GC GGT ATG CTG GCA GGC      2209
Ile Ala Leu Gly Ala Ser Thr Val Met Met G ly Gly Met Leu Ala Gly
        230                 235                 240

ACT ACA GAG TCT CCA GGC GAG TAC TTC TTC A GG GAC GGG AAG AGA CTG      2257
Thr Thr Glu Ser Pro Gly Glu Tyr Phe Phe A rg Asp Gly Lys Arg Leu
245                 250                 255                 260

AAG ACC TAC AGA GGT ATG GGC TCC ATC GAC G CC ATG CAA AAG ACT GAT      2305
Lys Thr Tyr Arg Gly Met Gly Ser Ile Asp A la Met Gln Lys Thr Asp
                265                 270                 275

GTC AAG GGT AAC GCC GCT ACC TCC CGT TAC T TC TCT GAG TCT GAC AAG      2353
Val Lys Gly Asn Ala Ala Thr Ser Arg Tyr P he Ser Glu Ser Asp Lys
            280                 285                 290

GTT CTG GTC GCT CAG GGT GTT ACT GGT TCT G TG ATC GAC AAG GGC TCC      2401
Val Leu Val Ala Gln Gly Val Thr Gly Ser V al Ile Asp Lys Gly Ser
        295                 300                 305

ATC AAG AAG TAC ATT CCA TAT CTG TAC AAT G GT CTA CAG CAC TCG TGC      2449
Ile Lys Lys Tyr Ile Pro Tyr Leu Tyr Asn G ly Leu Gln His Ser Cys
310                 315                 320

CAG GAT ATC GGT GTG CGC TCT CTA GTG GAG T TC AGA GAG AAG GTG GAC      2497
Gln Asp Ile Gly Val Arg Ser Leu Val Glu P he Arg Glu Lys Val Asp
325                 330                 335                 340

TCT GGC TCG GTC AGA TTT GAG TTC AGA ACT C CA TCT GCC CAG TTG GAG      2545
Ser Gly Ser Val Arg Phe Glu Phe Arg Thr P ro Ser Ala Gln Leu Glu
                345                 350                 355
```

-continued

```
GGT GGT GTG CAC AAC TTG CAC TCC TAC GAG A AG CGC CTA TTT GACTGAG   2597
Gly Gly Val His Asn Leu His Ser Tyr Glu L ys Arg Leu Phe Asp
        360                 365                 370

CACTAGGCCC ACACTATAGA AGTGGATCCG GGCGCGATGG CACCCATACT T TTATATTAT   2657

GTTGATTGAT GTACGTAAAC GATAGATATA ATAACAGACG CGGCATCTCA T TTGTATGCA   2717

ATATATCTGG AACATGGTTA TGCGTACTCA ACTGTATGTA CTACTTTATA T ACACAGCTC   2777

TGGGACACTT GGTGAGATAT ATGTTTCATT ATGTATGCCT CGCTATCGAA A GGTCTGGCA   2837

TTATGGGCTA CTGGGTCTAA GAGTCATGGC TTATGAGTAT TTATTTATTT A TTTCTCTTC   2897

CTTTTCATTA AACTCCTCGA GCTTCTTTCT GTAATACTGC TCTCTAGACT T CTCCACATC   2957

TGCTAATGAT GGTGGAAGTC GTTCGTTTTC CAAATCCGCT CTACGAGCGC G CTCGAAGTT   3017

AGACAGCGCC TCGTTCAGAC CTTCAGACCC GCGTGACAGC GCTCCACGAG G CAGCACGCC   3077

AGAATTCATT GTTTTTAGGT ACTGCACCTT ATCGCTCTCT TCTCTCAACA C GCTATACAT   3137

TCGGAAACC  TTGGCAATCG CCAATATTTT ACTGCGTAGT GCACGCCGTT T TGCATCATC   3197

GTCCAGAATA GACCGTTTTT TCTTCGATTT CTTGGAGCCA GGTATAACAG T TACAACCTG   3257

CTCAGTGTTT TTGGACTTCA ATGTAGCACC TAAGTCCTCC CTTATAACAA A AGTCTCTTC   3317

CTCCAATTCT TCTTCAGTAC AAATGTTTAA TATCGAAACC AACATTTCAG T CACTTTCTC   3377

GCCAACAAAT GGCAAAGACC AGGTGAATAC GTCCATGAAA TTCGGTAACC A ATACGGATG   3437

CTGTGACATG TTAAATTGTC TAATGTTCAT AACGTTATCC GAGTATTTTA G GACCGCGGC   3497

CTTGTTCTTG TAAGTGTCCA AGTAGTTGGG TGCGCTGAAC AACGTAAGTA A ACTAGGAAA   3557

GCCCAGATTC TTGGTATTCT TGTACATTCT GTAGCCCTGA TCTTGGGCTT C GTGGGCC    3616
```

(2) INFORMATION FOR SEQ ID NO: 8:

(i) SEQUENCE CHARACTERISTICS:
      (A) LENGTH: 151 amino acids
      (B) TYPE: amino acid
      (D) TOPOLOGY: linear (ii) MOLECULE TYPE: protein (xi) SEQUENCE DESCRIPTION: SEQ ID NO: 8:

```
Met Thr Tyr Arg Asp Ala Ala Thr Ala Leu G lu His Leu Ala Thr Tyr
 1               5                  10                  15

Ala Glu Lys Asp Gly Leu Ser Val Glu Gln L eu Met Asp Ser Lys Thr
            20                  25                  30

Arg Gly Gly Leu Thr Tyr Asn Asp Phe Leu V al Leu Pro Gly Lys Ile
        35                  40                  45

Asp Phe Pro Ser Ser Glu Val Val Leu Ser S er Arg Leu Thr Lys Lys
    50                  55                  60

Ile Thr Leu Asn Ala Pro Phe Val Ser Ser P ro Met Asp Thr Val Thr
65                  70                  75                  80

Glu Ala Asp Met Ala Ile His Met Ala Leu L eu Gly Gly Ile Gly Ile
                85                  90                  95

Ile His His Asn Cys Thr Ala Glu Glu Gln A la Glu Met Val Arg Arg
            100                 105                 110

Val Lys Lys Tyr Glu Asn Gly Phe Ile Asn A la Pro Val Val Gly
        115                 120                 125

Pro Asp Ala Thr Val Ala Asp Val Arg Arg M et Lys Asn Glu Phe Gly
    130                 135                 140

Phe Ala Gly Phe Pro Val Thr
```

145            150

(2) INFORMATION FOR SEQ ID NO: 9:

(i) SEQUENCE CHARACTERISTICS:
        (A) LENGTH: 371 amino acids
        (B) TYPE: amino acid
        (D) TOPOLOGY: linear (ii) MOLECULE TYPE: protein (xi) SEQUENCE DESCRIPTION: SEQ ID NO: 9:

```
Asp Asp Gly Lys Pro Thr Gly Lys Leu Gln G ly Ile Ile Thr Ser Arg
 1               5                  10                  15
Asp Ile Gln Phe Val Glu Asp Glu Thr Leu L eu Val Ser Glu Ile Met
                20                  25                  30
Thr Lys Asp Val Ile Thr Gly Lys Gln Gly I le Asn Leu Glu Glu Ala
            35                  40                  45
Asn Gln Ile Leu Lys Asn Thr Lys Lys Gly L ys Leu Pro Ile Val Asp
         50                  55                  60
Glu Ala Gly Cys Leu Val Ser Met Leu Ser A rg Thr Asp Leu Met Lys
 65                  70                  75                  80
Asn Gln Ser Tyr Pro Leu Ala Ser Lys Ser A la Asp Thr Lys Gln Leu
                85                  90                  95
Leu Cys Gly Ala Ala Ile Gly Thr Ile Asp A la Asp Arg Gln Arg Leu
            100                 105                 110
Ala Met Leu Val Glu Ala Gly Leu Asp Val V al Val Leu Asp Ser Ser
        115                 120                 125
Gln Gly Asn Ser Val Phe Gln Ile Asn Met I le Lys Trp Ile Lys Glu
    130                 135                 140
Thr Phe Pro Asp Leu Gln Val Ile Ala Gly A sn Val Val Thr Arg Glu
145                 150                 155                 160
Gln Ala Ala Ser Leu Ile His Ala Gly Ala A sp Gly Leu Arg Ile Gly
                165                 170                 175
Met Gly Ser Gly Ser Ile Cys Ile Thr Gln G lu Val Met Ala Cys Gly
            180                 185                 190
Arg Pro Gln Gly Thr Ala Val Tyr Asn Val T hr Gln Phe Ala Asn Gln
        195                 200                 205
Phe Gly Val Pro Cys Ile Ala Asp Gly Gly V al Gln Asn Ile Gly His
    210                 215                 220
Ile Thr Lys Ala Ile Ala Leu Gly Ala Ser T hr Val Met Met Gly Gly
225                 230                 235                 240
Met Leu Ala Gly Thr Thr Glu Ser Pro Gly G lu Tyr Phe Phe Arg Asp
                245                 250                 255
Gly Lys Arg Leu Lys Thr Tyr Arg Gly Met G ly Ser Ile Asp Ala Met
            260                 265                 270
Gln Lys Thr Asp Val Lys Gly Asn Ala Ala T hr Ser Arg Tyr Phe Ser
        275                 280                 285
Glu Ser Asp Lys Val Leu Val Ala Gln Gly V al Thr Gly Ser Val Ile
    290                 295                 300
Asp Lys Gly Ser Ile Lys Lys Tyr Ile Pro T yr Leu Tyr Asn Gly Leu
305                 310                 315                 320
Gln His Ser Cys Gln Asp Ile Gly Val Arg S er Leu Val Glu Phe Arg
                325                 330                 335
Glu Lys Val Asp Ser Gly Ser Val Arg Phe G lu Phe Arg Thr Pro Ser
            340                 345                 350
```

```
Ala Gln Leu Glu Gly Gly Val His Asn Leu His Ser Tyr Glu Lys Arg
        355                 360                 365

Leu Phe Asp
    370

(2) INFORMATION FOR SEQ ID NO: 10:

(i) SEQUENCE CHARACTERISTICS:
        (A) LENGTH: 2697 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: 5'UTR
        (B) LOCATION: 1..455

(ix) FEATURE:
        (A) NAME/KEY: CDS
        (B) LOCATION: 456..2033

(ix) FEATURE:
        (A) NAME/KEY: 3'UTR
        (B) LOCATION: 2034..2697

(xi) SEQUENCE DESCRIPTION: SEQ ID NO: 10:

ATCGATTTCA GGAGATTTTT GGTAGCATTA TTGAGGTCAT TAGAGGCGTT C TGTGACTTT      60

CGACGATTTG CACGCGCAGA AGAGGGCGTT CAACCAGCCT TTCGGATATT C CGGTTCGAG     120

TTATACCAGC AGGGATCAGC GCAGGCACTA GAGTGGCGGG TGCTAATAAG A GGAGCAGGT     180

CCTGGAACTG AAGTTGCAAG AGATAAGCAT TGCGCGGAGA AGGAGGCGGT T AGAGGGTGC     240

AAGCGAGCAG GATGGGGTCT TCGATGAACT TCCCGTCTGG GTATGTGAAC A AGCACACGC     300

TGCAGGCACA CCGGTAGGGC GAGTGCAGGG TGAAAAATAT ATATGCGCTC G AGAAGCGCT     360

GGGGATGAGT TCGTCTGCAA CGGCAGGCGG ATCTTCATCT GACAAAACCA G CTGCCTACA     420

TCAGTGCGAA GCTGTTCAGT GATAGAATAG GAGTA ATG GCT GCT GTT GAA CAA        473
                                       Met Ala Ala Val Glu Gln
                                         1               5

GTT TCT AGC GTG TTT GAC ACC ATT TTG GTG C TG GAC TTC GGG TCC CAG      521
Val Ser Ser Val Phe Asp Thr Ile Leu Val L eu Asp Phe Gly Ser Gln
             10                  15                  20

TAC TCG CAT CTG ATC ACG CGG CGG CTG CGT G AG TTT AAT GTG TAC GCG      569
Tyr Ser His Leu Ile Thr Arg Arg Leu Arg G lu Phe Asn Val Tyr Ala
         25                  30                  35

GAG ATG CTT CCG TGT ACG CAG AAG ATC AGC G AG CTG GGC TGG AAG CCA      617
Glu Met Leu Pro Cys Thr Gln Lys Ile Ser G lu Leu Gly Trp Lys Pro
     40                  45                  50

AAG GGT GTG ATT TTG TCA GGC GGG CCG TAC T CC GTG TAC GCG GCA GAT      665
Lys Gly Val Ile Leu Ser Gly Gly Pro Tyr S er Val Tyr Ala Ala Asp
 55                  60                  65                  70

GCT CCG CAC GTG GAC CGG GCG GTG TTC GAG T TG GGC GTT CCA ATT CTG      713
Ala Pro His Val Asp Arg Ala Val Phe Glu L eu Gly Val Pro Ile Leu
                 75                  80                  85

GGC ATC TGC TAC GGG CTA CAG GAG CTT GCG T GG ATA GCC GGC GCA GAG      761
Gly Ile Cys Tyr Gly Leu Gln Glu Leu Ala T rp Ile Ala Gly Ala Glu
             90                  95                 100

GTG GGG CGC GGC GAG AAG CGC GAG TAC GGG C GC GCG ACG CTG CAC GTG      809
```

```
                                                                         -continued Val Gly Arg Gly Glu Lys Arg Glu Tyr Gly A rg Ala Thr Leu His Val
        105                 110              115

GAG GAC AGC GCG TGC CCG CTG TTC AAC AAC G TG GAC AGC AGC ACG GTG       857
Glu Asp Ser Ala Cys Pro Leu Phe Asn Asn V al Asp Ser Ser Thr Val
120             125                 130

TGG ATG TCG CAC GGT GAC AAG CTG CAC GCA C TA CCT GCG GAT TTC CAC       905
Trp Met Ser His Gly Asp Lys Leu His Ala L eu Pro Ala Asp Phe His
135                 140                 145                 150

GTC ACT GCG ACG ACG GAG AAC TCT CCT TTC T GC GGG ATT GCA CAC GAC       953
Val Thr Ala Thr Thr Glu Asn Ser Pro Phe C ys Gly Ile Ala His Asp
                155                 160                 165

TCG AAG CCA ATC TTC GGG ATC CAG TTC CAC C CT GAG GTG ACG CAC TCC      1001
Ser Lys Pro Ile Phe Gly Ile Gln Phe His P ro Glu Val Thr His Ser
            170                 175                 180

TCG CAG GGG AAG ACG TTG CTG AAG AAC TTT G CG GTG GAG ATC TGC CAG      1049
Ser Gln Gly Lys Thr Leu Leu Lys Asn Phe A la Val Glu Ile Cys Gln
        185                 190                 195

GCC GCG CAG ACC TGG ACG ATG GAA AAC TTC A TT GAC ACC GAG ATC CAG      1097
Ala Ala Gln Thr Trp Thr Met Glu Asn Phe I le Asp Thr Glu Ile Gln
    200                 205                 210

CGG ATC CGG ACC CTT GTG GGC CCC ACC GCG G AA GTC ATC GGT GCT GTG      1145
Arg Ile Arg Thr Leu Val Gly Pro Thr Ala G lu Val Ile Gly Ala Val
215                 220                 225                 230

TCC GGC GGT GTC GAC TCG ACC GTC GCT GCG A AG CTG ATG ACC GAG GCC      1193
Ser Gly Gly Val Asp Ser Thr Val Ala Ala L ys Leu Met Thr Glu Ala
                235                 240                 245

ATC GGC GAC CGG TTC CAC GCG ATC CTG GTC G AC AAC GGT GTT CTG CGC      1241
Ile Gly Asp Arg Phe His Ala Ile Leu Val A sp Asn Gly Val Leu Arg
            250                 255                 260

CTC AAC GAA GCG GCC AAT GTG AAG AAA ATC C TC GGC GAG GGC TTG GGC      1289
Leu Asn Glu Ala Ala Asn Val Lys Lys Ile L eu Gly Glu Gly Leu Gly
        265                 270                 275

ATC AAC TTG ACT GTT GTT GAC GCC TCC GAA G AG TTC TTG ACG AAG CTC      1337
Ile Asn Leu Thr Val Val Asp Ala Ser Glu G lu Phe Leu Thr Lys Leu
    280                 285                 290

AAG GGC GTC ACG GAC CCT GAG AAG AAG AGA A AG ATC ATC GGT AAC ACC      1385
Lys Gly Val Thr Asp Pro Glu Lys Lys Arg L ys Ile Ile Gly Asn Thr
295                 300                 305                 310

TTC ATT CAT GTT TTT GAG CGC GAG GCA GCC A GG ATC CAG CCT AAG AAC      1433
Phe Ile His Val Phe Glu Arg Glu Ala Ala A rg Ile Gln Pro Lys Asn
                315                 320                 325

GGC GAG GAG ATT GAG TTC CTG TTG CAG GGT A CC CTA TAC CCT GAC GTT      1481
Gly Glu Glu Ile Glu Phe Leu Leu Gln Gly T hr Leu Tyr Pro Asp Val
            330                 335                 340

ATC GAG TCC ATT TCC TTT AAG GGC CCA TCT C AG ACG ATC AAG ACC CAC      1529
Ile Glu Ser Ile Ser Phe Lys Gly Pro Ser G ln Thr Ile Lys Thr His
        345                 350                 355

CAT AAC GTC GGT GGT CTT TTG GAC AAC ATG A AA CTG AAG CTC ATT GAG      1577
His Asn Val Gly Gly Leu Leu Asp Asn Met L ys Leu Lys Leu Ile Glu
    360                 365                 370

CCT TTG CGC GAG CTT TTC AAG GAC GAG GTG A GA CAC CTG GGA GAA CTA      1625
Pro Leu Arg Glu Leu Phe Lys Asp Glu Val A rg His Leu Gly Glu Leu
375                 380                 385                 390

TTG GGG ATC TCC CAC GAG TTG GTC TGG AGA C AT CCG TTC CCA GGC CCA      1673
Leu Gly Ile Ser His Glu Leu Val Trp Arg H is Pro Phe Pro Gly Pro
                395                 400                 405

GGT ATC GCC ATC CGT GTG CTA GGC GAG GTC A CC AAG GAG CAG GTG GAG      1721
Gly Ile Ala Ile Arg Val Leu Gly Glu Val T hr Lys Glu Gln Val Glu
            410                 415                 420
```

```
ATT GCC AGA AAG GCA GAC CAC ATC TAC ATC GAG GAG ATC AGG AAA GCA      1769
Ile Ala Arg Lys Ala Asp His Ile Tyr Ile Glu Glu Ile Arg Lys Ala
            425                 430                 435

GGT CTA TAC AAC AAG ATT TCT CAA GCT TTT GCT TGC TTG CTG CCT GTT      1817
Gly Leu Tyr Asn Lys Ile Ser Gln Ala Phe Ala Cys Leu Leu Pro Val
    440                 445                 450

AAG TCT GTG GGT GTC ATG GGT GAC CAG AGA ACC TAC GAC CAG GTC ATT      1865
Lys Ser Val Gly Val Met Gly Asp Gln Arg Thr Tyr Asp Gln Val Ile
455                 460                 465                 470

GCT CTA AGA GCA ATT GAG ACC ACG GAC TTC ATG ACT GCC GAC TGG TAT      1913
Ala Leu Arg Ala Ile Glu Thr Thr Asp Phe Met Thr Ala Asp Trp Tyr
                475                 480                 485

CCA TTT GAG CAC GAA TTC TTG AAG CAT GTC GCA TCC CGT ATT GTT AAC      1961
Pro Phe Glu His Glu Phe Leu Lys His Val Ala Ser Arg Ile Val Asn
        490                 495                 500

GAG GTT GAA GGT GTT GCC AGA GTC ACC TAC GAC ATA ACT TCT AAG CCT      2009
Glu Val Glu Gly Val Ala Arg Val Thr Tyr Asp Ile Thr Ser Lys Pro
            505                 510                 515

CCA GCT ACC GTT GAA TGG GAA TAATCACCCT TGGGATCCGC TGACTGGCTA         2060
Pro Ala Thr Val Glu Trp Glu
    520                 525

CTGTAATTCT ATGTAGTGGA TTAGTACGAT AAGTTACTTT TGTATGATAG ATGTAATCAC    2120

ATCTGGCTAT TAAAATGACT CAGCCGAGGT AAATCTAACG TCCCTTCACA AGGGTGTTCC    2180

TGTGTGGACT TCCGCCTGAA TTTTTATAGA TATATAGATA CTCTACTCAT GAACAACCTG    2240

CAACCGAATA AGCATTAGTG CCAGGAGAAG AGAACCGTGG AAATGGGGCA AGTAGAAAAA    2300

ATCATATTCC TTAAGAATAA GACAGTACCA GAGGACCATT ACGAGACGAT TTTTGAATCG    2360

AATGGCTTCC AGACTCACTT TGTACCCATA ATAACCCATG AACACCTGCC AGATGAGGTT    2420

CGCGGTCGAC TATCCGACGC GAATTACATG AAAAGGTTGA ATTGTTTGGT GGTAACCTCT    2480

CAGAGGACTG TGGAGTGTCT CTATGAGGAC GTTCTGCCCT CTCTTCCAGC TGAAGCACGC    2540

AAATCTCTTC TCAATACGCC AGTATTCGTG GTTGGGCGTG CCACTCAGGA ATTTATGGAG    2600

AGATGCGGCT TTACGGACGT GAGAGGGGGA TCTGAGACTG GTAATGGCGT TTTGCTAGCG    2660

GAGTTAATGT TAAATATGAT CCAGAAGGGC GATGGGG                             2697

(2) INFORMATION FOR SEQ ID NO: 11:

(i) SEQUENCE CHARACTERISTICS:
        (A) LENGTH: 525 amino acids
        (B) TYPE: amino acid
        (D) TOPOLOGY: linear (ii) MOLECULE TYPE: protein (xi) SEQUENCE DESCRIPTION: SEQ ID NO: 11:

Met Ala Ala Val Glu Gln Val Ser Ser Val Phe Asp Thr Ile Leu Val
1               5                   10                  15

Leu Asp Phe Gly Ser Gln Tyr Ser His Leu Ile Thr Arg Arg Leu Arg
            20                  25                  30

Glu Phe Asn Val Tyr Ala Glu Met Leu Pro Cys Thr Gln Lys Ile Ser
        35                  40                  45

Glu Leu Gly Trp Lys Pro Lys Gly Val Ile Leu Ser Gly Gly Pro Tyr
    50                  55                  60

Ser Val Tyr Ala Ala Asp Ala Pro His Val Asp Arg Ala Val Phe Glu
65                  70                  75                  80

Leu Gly Val Pro Ile Leu Gly Ile Cys Tyr Gly Leu Gln Glu Leu Ala
                85                  90                  95
```

```
Trp Ile Ala Gly Ala Glu Val Gly Arg Gly Glu Lys Arg Glu Tyr Gly
            100                 105                 110

Arg Ala Thr Leu His Val Glu Asp Ser Ala Cys Pro Leu Phe Asn Asn
            115                 120                 125

Val Asp Ser Ser Thr Val Trp Met Ser His Gly Asp Lys Leu His Ala
        130                 135                 140

Leu Pro Ala Asp Phe His Val Thr Ala Thr Thr Glu Asn Ser Pro Phe
145                 150                 155                 160

Cys Gly Ile Ala His Asp Ser Lys Pro Ile Phe Gly Ile Gln Phe His
                165                 170                 175

Pro Glu Val Thr His Ser Ser Gln Gly Lys Thr Leu Leu Lys Asn Phe
            180                 185                 190

Ala Val Glu Ile Cys Gln Ala Ala Gln Thr Trp Thr Met Glu Asn Phe
        195                 200                 205

Ile Asp Thr Glu Ile Gln Arg Ile Arg Thr Leu Val Gly Pro Thr Ala
        210                 215                 220

Glu Val Ile Gly Ala Val Ser Gly Gly Val Asp Ser Thr Val Ala Ala
225                 230                 235                 240

Lys Leu Met Thr Glu Ala Ile Gly Asp Arg Phe His Ala Ile Leu Val
            245                 250                 255

Asp Asn Gly Val Leu Arg Leu Asn Glu Ala Ala Asn Val Lys Lys Ile
            260                 265                 270

Leu Gly Glu Gly Leu Gly Ile Asn Leu Thr Val Val Asp Ala Ser Glu
        275                 280                 285

Glu Phe Leu Thr Lys Leu Lys Gly Val Thr Asp Pro Glu Lys Lys Arg
290                 295                 300

Lys Ile Ile Gly Asn Thr Phe Ile His Val Phe Glu Arg Glu Ala Ala
305                 310                 315                 320

Arg Ile Gln Pro Lys Asn Gly Glu Glu Ile Glu Phe Leu Leu Gln Gly
                325                 330                 335

Thr Leu Tyr Pro Asp Val Ile Glu Ser Ile Ser Phe Lys Gly Pro Ser
            340                 345                 350

Gln Thr Ile Lys Thr His His Asn Val Gly Gly Leu Leu Asp Asn Met
            355                 360                 365

Lys Leu Lys Leu Ile Glu Pro Leu Arg Glu Leu Phe Lys Asp Glu Val
370                 375                 380

Arg His Leu Gly Glu Leu Leu Gly Ile Ser His Glu Leu Val Trp Arg
385                 390                 395                 400

His Pro Phe Pro Gly Pro Gly Ile Ala Ile Arg Val Leu Gly Glu Val
                405                 410                 415

Thr Lys Glu Gln Val Glu Ile Ala Arg Lys Ala Asp His Ile Tyr Ile
            420                 425                 430

Glu Glu Ile Arg Lys Ala Gly Leu Tyr Asn Lys Ile Ser Gln Ala Phe
        435                 440                 445

Ala Cys Leu Leu Pro Val Lys Ser Val Gly Val Met Gly Asp Gln Arg
        450                 455                 460

Thr Tyr Asp Gln Val Ile Ala Leu Arg Ala Ile Glu Thr Thr Asp Phe
465                 470                 475                 480

Met Thr Ala Asp Trp Tyr Pro Phe Glu His Glu Phe Leu Lys His Val
            485                 490                 495

Ala Ser Arg Ile Val Asn Glu Val Glu Gly Val Ala Arg Val Thr Tyr
        500                 505                 510
```

```
Asp Ile Thr Ser Lys Pro Pro Ala Thr Val Glu Trp Glu
        515                 520                 525
```

(2) INFORMATION FOR SEQ ID NO: 12:

(i) SEQUENCE CHARACTERISTICS:
        (A) LENGTH: 1634 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY: 5'UTR
        (B) LOCATION: 1..519

(ix) FEATURE:
        (A) NAME/KEY: CDS
        (B) LOCATION: 520..1482

(ix) FEATURE:
        (A) NAME/KEY: 3'UTR
        (B) LOCATION: 1483..1634

(xi) SEQUENCE DESCRIPTION: SEQ ID NO: 12:

```
CCTCGAACAT CTATCTTCTG AGCTCGATAG TCTACGAAAT CGGCACACTA G CCTAATTGC        60

CGAGATGAAG AGCTCCAGGG AACCGTTAAA GATCTGATGT TCCATCTTCA A TCAGGACAA      120

ATGTTACGGG ATGTCCCTGA CGCCACAGAA GGTAGCCTGG TGGTCCAGAC A GAAAAAGAG      180

CCTACACCAA AGAAGAAACA TAACAAGAAA AAGCCTCCGC ATCGTTTTGG T AAATCATAA      240

TAGGCACGAT GCGCATATAC CCTGACCATC ATAGCGGTTC CCCCCGCTAA C TGCTCCGAG      300

CGGGTAACCC CATGTCACAA AGTGACTCTG TCTCTTCGTG GTAGGTGATG T CAAATTTTC      360

ACGACTTCCC ACCCCGATGA GCATCCGTAT TCCTTTTCAT CTAAATTCTA A TAGATGGCT      420

TATGGATTCT TATTGGCGAC TTACAAGCCT ATGTAGTTGG CTTCCCTCAA G TGTTCGTAG      480

TCTACCACCT CACACCCGGT CTAACAGCTT ACGAGAATA ATG GCT AC T AAT GCA         534
                                            Met Ala Thr Asn Ala
                                              1               5

ATC AAG CTT CTT GCG CCA GAT ATC CAC AGG G GT CTG GCA GAG CTG GTC       582
Ile Lys Leu Leu Ala Pro Asp Ile His Arg G ly Leu Ala Glu Leu Val
              10                  15                  20

GCT AAA CGC CTA GGC TTA CGT CTG ACA GAC T GC AAG CTT AAG CGG GAT       630
Ala Lys Arg Leu Gly Leu Arg Leu Thr Asp C ys Lys Leu Lys Arg Asp
          25                  30                  35

TGT AAC GGG GAG GCG ACA TTT TCG ATC GGA G AA TCT GTT CGA GAC CAG       678
Cys Asn Gly Glu Ala Thr Phe Ser Ile Gly G lu Ser Val Arg Asp Gln
      40                  45                  50

GAT ATC TAC ATC ATC ACG CAG GTG GGG TCC G GG GAC GTG AAC GAC CGA       726
Asp Ile Tyr Ile Ile Thr Gln Val Gly Ser G ly Asp Val Asn Asp Arg
  55                  60                  65

GTG CTG GAG CTG CTC ATC ATG ATC AAC GCT A GC AAG ACG GCG TCT GCG       774
Val Leu Glu Leu Leu Ile Met Ile Asn Ala S er Lys Thr Ala Ser Ala
70                  75                  80                  85

CGG CGA ATT ACG GCT GTG ATT CCA AAC TTC C CA TAC GCG CGG CAG GAC       822
Arg Arg Ile Thr Ala Val Ile Pro Asn Phe P ro Tyr Ala Arg Gln Asp
              90                  95                 100

CGG AAG GAT AAG TCA CGG GCG CCA ATT ACC G CG AAG CTC ATG GCG GAC       870
Arg Lys Asp Lys Ser Arg Ala Pro Ile Thr A la Lys Leu Met Ala Asp
         105                 110                 115
```

```
ATG CTG ACT ACC GCG GGC TGC GAT CAT GTC A TC ACC ATG GAC TTA CAC         918
Met Leu Thr Thr Ala Gly Cys Asp His Val I le Thr Met Asp Leu His
            120                 125                 130

GCT TCG CAA ATC CAG GGC TTC TTT GAT GTA C CA GTT GAC AAC CTT TAC         966
Ala Ser Gln Ile Gln Gly Phe Phe Asp Val P ro Val Asp Asn Leu Tyr
135                 140                 145

GCA GAG CCT AGC GTG GTG AAG TAT ATC AAG G AG CAT ATT CCC CAC GAC        1014
Ala Glu Pro Ser Val Val Lys Tyr Ile Lys G lu His Ile Pro His Asp
150                 155                 160                 165

GAT GCC ATC ATC ATC TCG CCG GAT GCT GGT G GT GCC AAA CGT GCG TCG        1062
Asp Ala Ile Ile Ile Ser Pro Asp Ala Gly G ly Ala Lys Arg Ala Ser
                170                 175                 180

CTT CTA TCA GAT CGC CTA AAC TTG AAC TTT G CG CTG ATT CAT AAG GAA        1110
Leu Leu Ser Asp Arg Leu Asn Leu Asn Phe A la Leu Ile His Lys Glu
                185                 190                 195

CGT GCA AAG GCA AAC GAA GTG TCC CGC ATG G TT CTG GTC GGC GAT GTT        1158
Arg Ala Lys Ala Asn Glu Val Ser Arg Met V al Leu Val Gly Asp Val
                200                 205                 210

ACC GAT AAA GTC TGC ATT ATC GTT GAC GAT A TG GCG GAT ACT TGT GGT        1206
Thr Asp Lys Val Cys Ile Ile Val Asp Asp M et Ala Asp Thr Cys Gly
        215                 220                 225

ACG CTG GCC AAG GCG GCA GAA GTG CTG CTA G AG CAC AAC GCG CGG TCT        1254
Thr Leu Ala Lys Ala Ala Glu Val Leu Leu G lu His Asn Ala Arg Ser
230                 235                 240                 245

GTG ATA GCC ATT GTT ACC CAC GGT ATC CTT T CA GGA AAG GCC ATT GAG        1302
Val Ile Ala Ile Val Thr His Gly Ile Leu S er Gly Lys Ala Ile Glu
                250                 255                 260

AAC ATC AAC AAT TCG AAG CTT GAT AGG GTT G TG TGT ACC AAC ACC GTG        1350
Asn Ile Asn Asn Ser Lys Leu Asp Arg Val V al Cys Thr Asn Thr Val
                265                 270                 275

CCA TTC GAG GAG AAG ATG AAG TTA TGC CCG A AG TTA GAT GTA ATT GAT        1398
Pro Phe Glu Glu Lys Met Lys Leu Cys Pro L ys Leu Asp Val Ile Asp
                280                 285                 290

ATC TCG GCA GTT CTT GCG GAA TCC ATT CGC C GT CTA CAC AAT GGT GAA        1446
Ile Ser Ala Val Leu Ala Glu Ser Ile Arg A rg Leu His Asn Gly Glu
                295                 300                 305

AGT ATC TCC TAC CTC TTT AAA AAC AAC CCA C TA TGATTTGCT TCTCGATGCT       1499
Ser Ile Ser Tyr Leu Phe Lys Asn Asn Pro L eu
310                 315                 320

GGCTTCTTGA GGGCCAATTT TGCCGTAGAG GTAGTATCCC TTCTTTTTAT A TTGACTATT      1559

TAACGAAGAC TATTTCTTCA TAAATGGACT TCGGCTTCAC TGTGAATCTC A CATGATATA     1619

GTTGTTTCAG AGACC                                                        1634

(2) INFORMATION FOR SEQ ID NO: 13:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO: 13:

Met Ala Thr Asn Ala Ile Lys Leu Leu Ala P ro Asp Ile His Arg Gly
 1               5                  10                  15

Leu Ala Glu Leu Val Ala Lys Arg Leu Gly L eu Arg Leu Thr Asp Cys
                20                  25                  30

Lys Leu Lys Arg Asp Cys Asn Gly Glu Ala T hr Phe Ser Ile Gly Glu
        35                  40                  45
```

```
Ser Val Arg Asp Gln Asp Ile Tyr Ile Ile Thr Gln Val Gly Ser Gly
 50                  55                  60

Asp Val Asn Asp Arg Val Leu Glu Leu Leu Ile Met Ile Asn Ala Ser
 65                  70                  75                  80

Lys Thr Ala Ser Ala Arg Arg Ile Thr Ala Val Ile Pro Asn Phe Pro
                 85                  90                  95

Tyr Ala Arg Gln Asp Arg Lys Asp Lys Ser Arg Ala Pro Ile Thr Ala
                100                 105                 110

Lys Leu Met Ala Asp Met Leu Thr Thr Ala Gly Cys Asp His Val Ile
                115                 120                 125

Thr Met Asp Leu His Ala Ser Gln Ile Gln Gly Phe Phe Asp Val Pro
                130                 135                 140

Val Asp Asn Leu Tyr Ala Glu Pro Ser Val Val Lys Tyr Ile Lys Glu
145                 150                 155                 160

His Ile Pro His Asp Asp Ala Ile Ile Ile Ser Pro Asp Ala Gly Gly
                165                 170                 175

Ala Lys Arg Ala Ser Leu Leu Ser Asp Arg Leu Asn Leu Asn Phe Ala
                180                 185                 190

Leu Ile His Lys Glu Arg Ala Lys Ala Asn Glu Val Ser Arg Met Val
                195                 200                 205

Leu Val Gly Asp Val Thr Asp Lys Val Cys Ile Ile Val Asp Asp Met
210                 215                 220

Ala Asp Thr Cys Gly Thr Leu Ala Lys Ala Ala Glu Val Leu Leu Glu
225                 230                 235                 240

His Asn Ala Arg Ser Val Ile Ala Ile Val Thr His Gly Ile Leu Ser
                245                 250                 255

Gly Lys Ala Ile Glu Asn Ile Asn Asn Ser Lys Leu Asp Arg Val Val
                260                 265                 270

Cys Thr Asn Thr Val Pro Phe Glu Glu Lys Met Lys Leu Cys Pro Lys
                275                 280                 285

Leu Asp Val Ile Asp Ile Ser Ala Val Leu Ala Glu Ser Ile Arg Arg
                290                 295                 300

Leu His Asn Gly Glu Ser Ile Ser Tyr Leu Phe Lys Asn Asn Pro Leu
305                 310                 315                 320

(2) INFORMATION FOR SEQ ID NO: 14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (PCR primer)

(iii) HYPOTHETICAL: NO (iv) ANTI-SENSE: NO (xi) SEQUENCE DESCRIPTION: SEQ ID NO: 14:

GATGCTAGAG ACCGCGGGGT GCAAC                                                25

(2) INFORMATION FOR SEQ ID NO: 15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear
```

(ii) MOLECULE TYPE: DNA (PCR primer)

(iii) HYPOTHETICAL: NO (iv) ANTI-SENSE: NO (xi) SEQUENCE DESCRIPTION: SEQ ID NO: 15:

TGTCCGCCAT GTCGTCTACA ATAATA                                                  26

(2) INFORMATION FOR SEQ ID NO: 16:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (PCR primer)

(iii) HYPOTHETICAL: NO (iv) ANTI-SENSE: NO (xi) SEQUENCE DESCRIPTION: SEQ ID NO: 16:

ATATCTTGAT GAAGACGTTC ACCGT                                                   25

(2) INFORMATION FOR SEQ ID NO: 17:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (PCR primer)

(iii) HYPOTHETICAL: NO (iv) ANTI-SENSE: NO (xi) SEQUENCE DESCRIPTION: SEQ ID NO: 17:

GATAATGACG GCTTGGCCGG GAAGA                                                   25

(2) INFORMATION FOR SEQ ID NO: 18:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (PCR primer)

(iii) HYPOTHETICAL: NO (iv) ANTI-SENSE: NO (xi) SEQUENCE DESCRIPTION: SEQ ID NO: 18:

GGCATCAACC TCGAGGAGGC GAACC                                                   25

(2) INFORMATION FOR SEQ ID NO: 19:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (PCR primer)

(iii) HYPOTHETICAL: NO (iv) ANTI-SENSE: NO (xi) SEQUENCE DESCRIPTION: SEQ ID NO: 19:

CAGACCGGCC TCGACCAGCA TCGCC                                                25

(2) INFORMATION FOR SEQ ID NO: 20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (PCR primer)

(iii) HYPOTHETICAL: NO (iv) ANTI-SENSE: NO (xi) SEQUENCE DESCRIPTION: SEQ ID NO: 20:

TGGACCGGGC GGTGTTCGAG TTGGG                                                25

(2) INFORMATION FOR SEQ ID NO: 21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (PCR primer)

(iii) HYPOTHETICAL: NO (iv) ANTI-SENSE: NO (xi) SEQUENCE DESCRIPTION: SEQ ID NO: 21:

AGGCTGGATC CTGGCTGCCT CGCGC                                                25

GENES OF PURINE BIOSYNTHESIS FROM ASHBYA GOSSYPII AND THE USE THEREOF IN MICROBIAL RIBOFLAVIN SYNTHESIS

The present invention relates to genes of purine biosynthesis from *Ashbya gossypii* and to the use thereof in riboflavin synthesis.

Vitamin B2, also called riboflavin, is essential for humans and animals. Vitamin B2 deficiency is associated with inflammations of the mucous membranes of the mouth and throat, itching and inflammations in the skin folds and similar cutaneous lesions, conjunctival inflammations, reduced visual accuracy and clouding of the cornea. Babies and children may experience cessation of growth and loss of weight. Vitamin B2 therefore has economic importance, especially as vitamin supplement in cases of vitamin deficiency and as supplement to animal feed. It is also employed for coloring foodstuffs, for example in mayonnaise, icecream, blancmange etc.

Vitamin B2 is prepared either chemically or microbially (see, for example, Kurth et al. (1996) riboflavin, in: Ullmann's Encyclopedia of industrial chemistry, VCH Weinheim). In the chemical preparation process, riboflavin is, as a rule, obtained as pure final product in multistage processes, it being necessary to employ relatively costly starting materials such as, for example, D-ribose. An alternative to the chemical synthesis of riboflavin is the preparation of this substance by microorganisms. The starting materials used in this case are renewable raw materials such as sugars or vegetable oils. The preparation of riboflavin by fermentation of fungi such as *Eremothecium ashbyii* or *Ashbya gossypii* is known (The Merck Index, Windholz et al., eds. Merck & Co., page 1183, 1983), but yeasts such as, for example, Candida, Pichia and Saccharomyces, or bacteria such as, for example, Bacillus, clostridia or corynebacteria, have also been described as riboflavin producers.

EP 405370 describes riboflavin-overproducing bacterial strains obtained by transformation of the riboflavin biosynthesis genes from *Bacillus subtilis*. These genes described therein, and other genes involved in vitamin B2 biosynthesis from prokaryotes are unsuitable for a recombinant riboflavin preparation process using eukaryotes such as, for example, *Saccharomyces cerevisiae* or *Ashbya gossypii*.

DE 44 20 785 describes six riboflavin biosynthesis genes from *Ashbya gossypii*, and microorganisms transformed with these genes, and the use of such microorganisms for riboflavin synthesis.

It is possible with these processes to generate producer strains for microbial riboflavin synthesis. However, these producer strains often have metabolic limitations which cannot be eliminated by the inserted biosynthesis genes or are sometimes induced thereby. Such producer strains are sometimes unable to provide sufficient substrate for saturating some steps in the biosynthesis, so that the biosynthetic capacity of some segments of metabolism cannot be fully exploited.

It is therefore desirable to enhance further sections of metabolic pathways, thereby to eliminate metabolic bottlenecks and thus further optimize the microorganism employed for the microbial riboflavin synthesis (producer strains) in respect of their ability for riboflavin synthesis. It is desirable to identify the enhancing sections of the complex metabolism and to enhance these in a suitable way.

The present invention relates to novel proteins of purine biosynthesis, the genes therefor and the use thereof for microbial riboflavin synthesis.

Purine metabolism (for a review, see, for example, Voet, D. and Voet, J. G., 1994, Biochemie, VCH Weinheim, pages 743–771; Zalkin, H. and Dixon, J. E., 1992, De novo purine nucleotide biosynthesis, in: Progress in nucleic acid research and molecular biology, Vol. 42, pages 259–287, Academic Press) is a part of the metabolism which is essential for all life forms. Faulty purine metabolism may in humans lead to serious diseases (e.g. gout). Purine metabolism is moreover an important target for treating oncoses and viral infections. Numerous publications have appeared describing substances which intervene in purine metabolism for these indications (as review, for example Christopherson, R. I. and Lyons, S. D., 1990, Potent inhibitors of de novo pyrimidine and purine biosynthesis as chemotherapeutic agents, Med. Res. Reviews 10, pages 505–548).

Investigations on the enzymes involved in purine metabolism (Smith, J. L., Enzymes in nucleotide synthesis, 1995, Curr. Opinion Struct. Biol. 5, 752–757) aim to develop novel immunosuppressives, antiparasitic or antiproliferative medicines (Biochem. Soc. Transact. 23, pages 877–902, 1995).

These medicines are normally not naturally occurring purines, pyrimidines or compounds derived therefrom.

The present invention relates to a protein having the polypeptide sequence depicted in SEQ ID NO:2 or a polypeptide sequence obtainable from SEQ ID NO:2 by substitution, insertion or deletion of up to 15% of the amino acids, and having the enzymatic activity of a phosphoribosyl-pyrophosphate synthetase.

The sequence depicted in SEQ ID NO:2 is the gene product of the KPR1 gene (SEQ ID No:1) obtained from *Ashbya gossypii*.

The invention further relates to a protein having the polypeptide sequence depicted in SEQ ID NO:5 or a polypeptide sequence obtainable from SEQ ID NO:5 by substitution, insertion or deletion of up to 10% of the amino acids, and having the enzymatic activity of a glutamine-phosphoribosyl-pyrophosphate amidotransferase.

The sequence depicted in SEQ ID NO:5 is the gene product of the ADE4 gene (SEQ ID NO:3) obtained from *Ashbya gossypii*.

The invention further relates to a protein having the polypeptide sequence depicted in SEQ ID NO:8 or a polypeptide sequence obtainable from SEQ ID NO:8 by substitution, insertion or deletion of up to 20% of the amino acids, and having the enzymatic activity of an IMP dehydrogenase.

The sequence depicted in SEQ ID NO:8 and 9 is the gene product of the GUA1 gene (SEQ ID NO:7) obtained from *Ashbya gossypii*.

The invention further relates to a protein having the polypeptide sequence depicted in SEQ ID NO:11 or a polypeptide sequence obtainable from SEQ ID NO:11 by substitution, insertion or deletion of up to 10% of the amino acids, and having the enzymatic activity of a GMP synthetase.

The sequence depicted in SEQ ID NO:11 is the gene product of the GUA2 gene (SEQ ID NO:10) obtained from *Ashbya gossypii*.

The invention further relates to a protein having the polypeptide sequence depicted in SEQ ID NO:13 or a polypeptide sequence obtainable from SEQ ID NO:13 by substitution, insertion or deletion of up to 10% of the amino acids, and having the enzymatic activity of a phosphoribosyl-pyrophosphate synthetase.

The sequence depicted in SEQ ID NO:13 is the gene product of the KPR2 gene (SEQ ID NO:12) obtained from *Ashbya gossypii*.

These gene products mentioned can be modified by conventional methods of gene technology, such as site-directed mutagenesis, so that particular amino acids are replaced, additionally inserted or deleted. Amino acid residues are normally (but not exclusively) replaced by those of similar volume, charge or hydrophilicity/hydrophobicity in order not to lose the enzymatic properties of the gene products. In particular, modifications of the amino acid sequence in the active center frequently results in a drastic alteration in the enzymatic activities. However, modifications of the amino acid sequence and other, less essential sites are often tolerated.

It is possible with the novel proteins 1. for up to 15, preferably up to 10 and particularly preferably up to 5, % of the amino acids to be modified, by comparison with sequences depicted in the sequence listing, in the case of the gene product of the AgKPR1 gene;
2. for up to 10 and particularly preferably up to 5% of the amino acids to be modified, by comparison with the sequences depicted in the sequence listing, in the case of the gene product of the AgADE4 gene;
3. for up to 20, preferably up to 15, particularly preferably up to 10 and especially preferably up to 5, % of the amino acids to be modified, by comparison with the sequences depicted in the sequence listing, in the case of the gene product of the AgGUA1 gene;
4. for up to 10 and particularly preferably up to 5% of the amino acids to be modified, by comparison with the sequences depicted in the sequence listing, in the case of the gene product of the AgGUA2 gene;
5. for up to 10%, preferably up to 7% and particularly preferably up to 5%, of the amino acids to be modified, by comparison with the sequences depicted in the sequence listing, in the case of the gene product of the AgKPR2 gene.

Preferred proteins are those which, while they still have the relevant enzymatic activity, have altered regulation. Many of these enzymes are subject to a strong control of the activity by intermediates and final products (feedback inhibition). This leads to the activity of the enzymes being restricted as soon as sufficient final product is present.

However, in the case of producer strains, this economic control in the physiological state often results in it being impossible to increase the productivity beyond a certain limit. Elimination of such feedback inhibition results in the enzymes retaining their activity, irrespective of the final product concentration, and thus metabolic bottlenecks are bypassed. This in the end leads to a marked increase in riboflavin biosynthesis.

Preferred novel proteins are those no longer inhibited by secondary products of metabolic pathways (derived from products of the enzymes). Particularly preferred novel proteins are those no longer inhibited by intermediates of purine biosynthesis, in particular by purine bases, purine nucleosides, purine nucleotide 5'-monophosphates or purine nucleotide 5'-diphosphates or purine nucleotide 5'-triphosphates. Particularly preferred novel proteins are those with subsequent modifications of the amino acid sequence and all combinations of amino acid sequence modifications which comprise these subsequent modifications.

Modifications of the amino acid sequence of the AgKPR1 gene product:

Lysine at position 7 replaced by valine
Aspartate at position 52 replaced by histidine
Leucine at position 133 replaced by isoleucine
Aspartate at position 186 replaced by histidine
Alanine at position 193 replaced by valine
Histidine at position 196 replaced by glutamine Modifications of the amino acid sequence of the AgADE4 gene product:

Aspartate at position 310 replaced by valine
Lysine at position 333 replaced by alanine
Alanine at position 417 replaced by tryptophan The following Examples describe the preparation of the novel proteins and nucleic acids and the use thereof for producing microorganisms with increased riboflavin synthesis.

EXAMPLE 1

Production of a Genomic Gene Bank from *Ashbya gossypii* ATCC10895

Genomic DNA from *Ashbya gossypii* ATCC10895 can be prepared by conventional methods as described, for example, in WO9703208. The genomic gene bank can be constructed starting from this DNA by conventional methods (e.g. Sambrook, J. et al. (1989) Molecular cloning: a laboratory manual, Cold Spring Harbor Laboratory Press or Ausubel, F. M. et al. (1994) Current protocols in molecular biology, John Wiley and sons) in any suitable plasmids or cosmids, such as, for example, SuperCos1 (Stratagene, La Jolla, USA).

EXAMPLE 2

Cloning of the Gene for PRPP Synthetase from *Ashbya gossypii* ATCC10895 (AgKPR1)

Cloning of the gene for PRPP synthetase from *Ashbya gossypii* (AgKPR1) can take place in two steps. In the first step, it is possible with the following oligonucleotides to amplify a defined region of the KPR1 gene from genomic DNA from *Ashbya gossypii* by PCR:

KPR5 (SEQ ID NO:14): 5'-GATGCTAGAGACCGCGGGGTG-CAAC-3'

KPR3 (SEQ ID NO:15): 5'-TGTCCGCCATGTCGTCTA-CAATAATA-3'

The PCR can be carried out by a conventional method. The resulting 330 bp DNA fragment can be cloned by conventional methods into the vector pGEMT (Promega, Madison, USA) and be sequenced.

A genomic cosmid gene bank can be screened by conventional methods using this nucleotide sequence as probe. A 1911 bp PstI-HindIII fragment of a cosmid which gives a signal with this probe can then be subcloned into the vector pBluescript SK+ (Stratagene, La Jolla, USA). The KPR1 gene and incomplete ORFs which show homology with the UBC6 and UBP9 genes of *Saccharomyces cerevisiae* are located on this fragment.

The PRPP synthetase KPR2 and the putative PRPP synthetase KPR4 from *Saccharomyces cerevisiae* are the enzymes which are most closely related, with similarities of 80.2% and 79.6% respectively, to the PRPP synthetase from *Ashbya gossypii*. The KPR2 and KPR4 genes from *Saccharomyces cerevisiae* have 67.6% and 67.8%, respectively, similarity with the KPR1 gene from *Ashbya gossypii*. Other enzymes and genes from other organisms are distinctly more different from the KPR1 gene and from the PRPP synthetase from *Ashbya gossypii*.

The sequence comparisons can be carried out, for example, with the Clustal algorithm with the aid of the PAM250 weighting table or the Wilbur-Lipman DNA alignment algorithm (as implemented, for example, in the MegAlign 3.06 program package supplied by DNAstar). It is not possible with the oligonucleotide pair described to amplify the genes for the different PRPP synthetases from *Saccharomyces cerevisiae*.

It is also possible to use the probe to find a further clone from the gene bank. This second clone showed a gene which likewise codes for a PRPP synthetase. This gene is called AgKPR2 and is distinctly different from AgKPR1. AgKPR2 shows 66% identity with AgKPR1 at the amino acid level. The AgKPR2 gene (SEQ ID NO:12) was compared with all proteins of the Swissprot database. The maximum similarity shown by this protein (88% identity and 95% similarity) is with the KPR3 gene product from *Saccharomyces cerevisiae*. The gene product of the AgKPR1 gene is responsible for the predominant part of the PRPP synthetase activity in *Ashbya gossypii*. Disruption of the AgKPR1 gene of *Ashbya gossypii* (analogous to the disruption of other Ashbya genes as in the descriptions in Examples 6–8) results in a distinctly reduced enzyme activity: in place of 22 U/mg of protein now only 3 U/mg of protein. See Example 13 for the analysis. Examples 11, 13 and 15 relate to the AgKPR1 gene, but studies of these types can also be carried out with AgKPR2.

EXAMPLE 3

Cloning of the Gene for Glutamine-PRPP Amidotransferase from *Ashbya gossypii* ATCC10895 (AgADE4)

The cloning of the gene for glutamine-PRPP amidotransferase from *Ashbya gossypii* (AgADE4) can take place in two steps.

In the first step, it is possible with the following oligonucleotides to amplify a defined region of the AgADE4 gene from genomic DNA of *Ashbya gossypii* by PCR:

ADE4A (SEQ ID NO:16): 5'-ATATCTTGATGAAGACGTTCAC-CGT-3'

ADE4B (SEQ ID NO:17): 5'-GATAATGACGGCTTGGCCGG-GAAGA-3'

The PCR can be carried out by a conventional method. The resulting 360 bp DNA fragment can be cloned by conventional methods into the vector pGEMT (Promega, Madison, USA) and then be sequenced.

This sequence can be used as probe to screen a genomic cosmid gene bank by conventional methods. It is then possible to subclone a 5369 bp HindIII fragment from a cosmid which gives a signal with this probe into the vector pBluescript SK+ (Stratagene, La Jolla, USA). The AgADE4 gene and the gene for the Ashbya homolog for the mitochondrial ABC transporter ATM1 from *Saccharomyces cerevisiae* and another open reading frame whose function is unknown are located on this fragment.

The AgADE4 gene product (glutamine-PRPP amidotransferase) shows the most evident similarity with the ADE4 gene products from *Saccharomyces cerevisiae* and *Saccharomyces kluyveri* (81% and 86.3% respectively). The corresponding genes show only 68.8% and 72%, respectively, homology, however. The similarity with other glutamine-PRPP amidotransferases is distinctly less (e.g. only 27.5% similarity with the corresponding enzyme from *Bacillus subtilis*). The sequence comparisons can be carried out as described in Example 2.

It is not possible with the described pair of oligonucleotides to amplify the ADE4 genes from *Saccharomyces cerevisiae* or *Saccharomyces kluyveri*.

EXAMPLE 4

Cloning of the Gene for Inosine-monophosphate Dehydrogenase from *Ashbya gossypii* ATCC10895 (AgGUA1)

Cloning of the gene for inosine-monophosphate dehydrogenase from *Ashbya gossypii* (AgGUA1) can take place in two steps.

In the first step, it is possible with the following oligonucleotides to amplify a defined region of the AgGUA1 gene from genomic DNA from *Ashbya gossypii* by PCR:

IMP5 (SEQ ID NO:18): 5'-GGCATCAACCTCGAGGAGGC-GAACC-3'

IMP3 (SEQ ID NO:19): 5'-CAGACCGGCCTCGACCAG-CATCGCC-3'

The PCR can be carried out by a conventional method. The resulting 230 bp DNA fragment can be cloned by conventional methods into the vector pGEMT (Promega, Madison, USA) and then be sequenced.

This sequence can be used as probe to screen a genomic cosmid gene bank by conventional methods. A 3616 bp ApaI fragment from a cosmid which gives a signal with this probe can be subloned into the vector pBluescript SK+ (Stratagene, La Jolla, USA). The coding region of the AgGUA1 gene is 1569 bp long and is interrupted by a 161 bp-long intron. The intron boundaries (5' splice site AGG-TATGT and 3' splice site CAG) can be verified by cloning and sequencing of AgGUA1cDNA.

AgGUA1 is the first gene decribed from *Ashbya gossypii* having an intron.

The AgGUA1 gene product (IMP dehydrogenase) shows the most evident similarity with the 4 IMP dehydrogenases from *Saccharomyces cerevisiae* (similarities between 67% and 77.2%). The similarity with other IMP dehydrogenases is distinctly less. The sequence comparisons can be carried out as described in Example 2. *Ashbya gossypii* appears to have only one gene for this enzyme. This can be shown by Southern blotting with genomic DNA from *Ashbya gossypii* using the abovementioned probe.

The gene from *Saccharomyces cerevisiae* which codes for the IMP dehydrogenase (IMH3) which has most similarity with the AgGUA1 gene product has a similarity of 70.2% with the AgGUA1 gene. It is not possible with the described pair of oligonucleotides to amplify this gene from *Saccharomyces cerevisiae*.

EXAMPLE 5

Cloning of the Gene for Guanosine-monophosphate Synthetase from *Ashbya gossypii* ATCC10895 (AgGUA2)

Cloning of the gene for guanosine-monophosphate synthetase from *Ashbya gossypii* (AgGUA2) can take place in two steps.

In the first step, it is possible with the following oligonucleotides to amplify a defined region of the AgGUA2 gene from genomic DNA from *Ashbya gossypii* by PCR:

GUA2A (SEQ ID NO:20): 5'-TGGACCGGGCGGTGTTCGAGT-TGGG-3'

GUA2B (SEQ ID NO:21): 5'-AGGCTGGATCCTGGCTGC-CTCGCGC-3'

The PCR can be carried out by a conventional method. The resulting 750 bp DNA fragment can be cloned by conventional methods into the vector pBluescript SK+ (Stratagene, La Jolla, USA) and then be sequenced.

This sequence can be used as probe to screen a genomic cosmid gene bank by conventional methods. A 2697 bp ClaI-EcoRV fragment from a cosmid which gives a signal with this probe can then be subcloned into the vector pBluescript SK+ (Stratagene, La Jolla, USA).

The AgGUA2 gene product (GMP synthetase) shows the most evident similarity with GMP synthetase from *Saccharomyces cerevisiae* (similarity 86.6%). The genes for the GMP synthetases from *Saccharomyces cerevisiae* and *Ashbya gossypii* show 71.2% homology. The similarity of the AgGUA2 gene product with other GMP synthetases is distinctly less. The sequence comparisons can be carried out as described in Example 2.

It is not possible with the described pair of oligonucleotides to amplify the GMP synthetase gene from *Saccharomyces cerevisiae*.

EXAMPLE 6

Disruption of the AgADE4 Gene from *Ashbya gossypii* ATCC10895

Disruption of a gene means destroying the functionality of a genomic copy of the gene either by (a) deleting part of the gene sequence, or by (b) interrupting the gene by inserting a piece of foreign DNA into the gene or by (c) replacing part of the gene by foreign DNA. Any foreign DNA can be used, but it is preferably a gene which brings about resistance to any suitable chemical. Any suitable resistance genes can be used for disruption of genes.

A gene which confers resistance to G418 can be used to disrupt the AgADE4 gene from *Ashbya gossypii* ATCC10895. It is possible for this to be the kanamycin resistance gene from TN903 under the control of the TEF promoter of *Ashbya gossypii* (see, for example, Yeast 10, pages 1793–1808, 1994, WO9200379). The gene is flanked 5' and 3' by several cleavage sites for restriction endonucleases, thus constructing a cassette which allows any desired constructions of gene disruptions by conventional methods of in vitro manipulation of DNA.

The internal HincII fragment of AgADE4 (between positions 2366 and 2924) can be replaced by a resistance cassette as outlined above. The resulting construct is called ade4::G418.

The resulting plasmid can be replicated in *E. coli*. The BamHI/BglII fragment of the construct ade4::G418 can be prepared, purified by agarose gel electrophoresis and subsequent elution of the DNA from the gel (see Proc. Natl. Acad. Sci. USA 76, 615–619, 1979) and employed for transforming *Ashbya gossypii*.

*Ashbya gossypii* can be transformed by protoplast transformation (Gene 109, 99–105, 1991), but preferably by electroporation (BioRad Gene Pulser, conditions: cuvettes with slit widths 0.4 mm, 1500 V, 25 $\mu$F, 100 $\Omega$). Transformed cells are selected from G418-containing solid medium.

Resulting G418-resistant clones can be examined by conventional methods of PCR and Southern blot analysis to find whether the genomic copy of the AgADE4 gene is in fact destroyed. Clones whose AgADE4 gene is destroyed are purine-auxotrophic.

EXAMPLE 7

Disruption of the AgGUA1 Gene from *Ashbya gossypii* ATCC10895

See Example 6 for a description of the principle of disruption of genes, the use of a resistance cassette and the transformation of *Ashbya gossypii*.

The internal XhoI/KpnI fragment of AgGUA1 (between positions 1620 and 2061) can be replaced by a resistance cassette as outlined above. The resulting construct is called gua1::G418.

The resulting plasmid can be replicated in *E. coli*. The XbaI/BamHI fragment of the construct gua1::G418 can be prepared, purified by agarose gel electrophoresis and subsequent elution of the DNA from the gel and employed for transforming *Ashbya gossypii*.

Resulting G418-resistant clones can be examined by conventional methods of PCR and Southern blot analysis to find whether the genomic copy of the AgGUA1 gene is in fact destroyed. Clones hose AgGUA1 gene is destroyed are guanine-auxotrophic.

EXAMPLE 8

Disruption of the AgGUA2 Gene from *Ashbya gossypii* ATCC10895

See Example 6 for a description of the principle of disruption of genes, the use of a resistance cassette and the transformation of *Ashbya gossypii*.

The internal SalI fragment of AgGUA2 (between positions 1153 and 1219) can be replaced by a resistance cassette as outlined above. The resulting construct is called gua2::G418.

The resulting plasmid can be replicated in *E. coli*. The XbaI/BamHI fragment of the construct gua2::G418 can be prepared, purified by agarose gel electrophoresis and subsequent elution of the DNA from the gel and employed for transforming *Ashbya gossypii*.

Resulting G418-resistant clones can be examined by conventional methods of PCR and Southern blot analysis to find whether the genomic copy of the AgGUA2 gene is in fact destroyed. Clones whose AgGUA2 gene is destroyed are guanine-auxotrophic.

EXAMPLE 9

Cloning of the GAP Promoter from *Ashbya gossypii*

The gene for glyceraldehyde-3-phosphate dehydrogenase from *Ashbya gossypii* (AgGAP) can be cloned by generally customary screening of a genomic *Ashbya gossypii* cosmid gene bank (see Example 1, with a probe which was constructed from information on the sequence of the GAP gene from *Saccharomyces cerevisiae*).

The 5' nontranslated region of the gene (−373 to −8 region relative to the translation start) was assumed to be promoter. 2 cleavage sites for the restriction endonuclease NotI were inserted flanking this sequence. In this region there are the bona fide TATA Box (nt 224–230), two sequence sections (nt 43–51 and 77–85) which correspond to the GCR1 binding element, and a sequence section (nt 9–20) whose complement partially corresponds to the RAP1 binding element of *Saccharomyces cerevisiae* (see, for example, Johnston, M. and Carlson, M. (1992) pp.193–281 in The molecular biology and cellular biology of the yeast Saccharomyces: Gene expression, Cold Spring Harbor Laboratory Press). The promoter cassette constructed in this way can be placed as easily portable expression signal in front of any desired gene for overexpression in *Ashbya gossypii* and results in pronounced overexpression of genes in *Ashbya gossypii*, as shown in Example 11.

EXAMPLE 10

Construction of Plasmids Having Genes Under the Control of the GAP Promoter from *Ashbya gossypii*

In order to introduce the GAP promoter cassette 5' of the coding region of the AgADE4 gene, a unique NotI cleavage site (recognition sequence GCGGCCGC) was inserted by conventional methods (e.g. Glover, D. M. and Hames, B. D. (1995) DNA cloning Vol.1, IRL press) 8 bp 5' of the ATG start codon.

The GAP promoter cassette can then be inserted via NotI into this position. An analogous procedure can be used for cloning the GAP promoter cassette 5' of the coding region of the genes AgKPR1, AgGUA1, AgGUA2 and for variants of the genes AgADE4, AgKPR1, AgGUA1 and AgGUA2.

Expression of the genes which harbor the GAP promoter cassette 5' of the coding region in *Ashbya gossypii* is controlled by the GAP promoter.

EXAMPLE 11

Overexpression of Genes in *Ashbya gossypii* Under the Control of the GAP Promoter Transformation of *Ashbya gossypii* with the DNA constructs described in Example 10 can be carried out as described in Example 6. The recipient clones can preferably, but not exclusively, be those which, before the transformation to be carried out here, harbor a disruption of the gene to be overexpressed. Thus, for example, the *Ashbya gossypii* mutant which is described in Example 6 and harbors an ade4::G418 mutation can be transformed with a GAP-ADE4 construct described in Example 10. Integration of the construct into the genome can be verified by Southern blot analysis. The resulting clones no longer have a G418 resistance gene (and are thus G418-sensitive) and are purine-prototrophic. Overexpression can be demonstrated by Northern blot analysis or detection of the enzymatic activity (as described in Example 12). On expression of the AgADE4 gene under the natural promoter, 0.007 U/mg of protein can be detected. On expression of the AgADE4 gene under the GAP promoter, 0.382 U/mg of protein can be detected.

A sequence section of the coding region of the AgADE4 gene can be used as probe. An analogous procedure can be used with AgKPR1, AgGUA1, AgGUA2 and for variants of all these genes. In addition, combinations of one of these genes together with other genes can be introduced in this way into the genome of *Ashbya gossypii*.

The wild type *Ashbya gossypii* has a specific PRPP synthetase activity of 22 U/mg of protein (see Example 13 for analysis of the PRPP synthetase). On expression of the AgKPR1 gene with the GAP promoter, 855 U/mg of protein is detectable.

EXAMPLE 12

Variants of the AgADE4 gene product (glutamine-PRPP amidotransferase) no longer subject to feedback inhibition by purines or intermediates of purine synthesis.

Glutamine-PRPP amidotransferases are subject to feedback inhibition by purine nucleotides. This inhibition is found in numerous organisms (see, for example, Switzer, R. L. (1989) Regulation of bacterial Glutamine Phosphoribosylpyrophosphate Amidotransferase, in: Allosteric enzymes pp. 129–151, CRC press, Boca Raton).

The glutamine-PRPP amidotransferase from *Ashbya gossypii* is likewise inhibited by AMP or GMP (see Figure). The activity of glutamine-phosphoribosyl-pyrophosphate amidotransferase from *Ashbya gossypii* can be measured as described in Messenger and Zalkin (1979) J. Biol. Chem. 254, pages 3382–3392.

Modified glutamine-phosphoribosyl-pyrophosphate amidotransferases no longer inhibited by purines can be constructed. It is evident that overexpression of such deregulated enzymes will enhance purine metabolism distinctly more than overexpression of enzymes subject to feedback inhibition. Alterations in the sequence of the AgADE4 gene can be brought about by conventional methods (e.g. Glover, D. M. and Hames, B. D. (1995) DNA cloning Vol.1, IRL press). It is possible, for example, for the following amino acids in glutamine-phosphoribosyl-pyrophosphate amidotransferase to be replaced:

The codon which codes for aspartate at position 310 can be replaced by a codon which codes for valine. The codon which codes for lysine at position 333 can be replaced by a codon which codes for alanine. The codon which codes for alanine at position 417 can be replaced by a codon which codes for tryptophan. It is additionally possible to construct AgADE4 genes which harbor combinations of these substitutions.

All enzymes which carry D310V, K333A, A417W or any combination of substitutions which comprise D310V or K333A show diminished feedback inhibition by AMP and GMP (see Figure). This can be shown, for example, by expressing the enzymes in *Ashbya gossypii* (see Example 11).

EXAMPLE 13

Variants of the AgKPR1 gene product (PRPP synthetase) no longer subject to feedback inhibition by purines or intermediates of purine synthesis.

PRPP synthetases are subject to feedback inhibition by purines, pyrimidines and amino acids. This inhibition is found in numerous organisms (see, for example, Gibson, K. J. et al. (1982) J. Biol. Chem. 257, 2391–2396; Tatibana, M. et al. (1995) Adv., Enzyme Regul. 35, 229–249 and papers quoted therein).

In clinical medical research there are descriptions of cases of hereditary gout based on enhanced purine biosynthesis. The molecular cause thereof is what is called superactivity of human PRPP synthetase (see, for example, Amer. J. Med. 55 (1973) 232–242; J. Clin. Invest. 96 (1995) 2133–2141; J. Biol. 268 (1993) 26476–26481). The basis thereof may be a mutation which leads to the enzyme no longer being subject to feedback inhibition by purines.

The activity of the PRPP synthetase from *Ashbya gossypii* can be measured as described in Anal. Biochem. 98 (1979) 254–263 or J. Bacteriol. 174 (1992) 6852–6856. The specific activity (U/mg) is defined via the amount of resulting product (nmol/min/g of protein).

It is possible to construct modified PRPP synthetases no longer inhibited by purines. It is evident that overexpression of such deregulated enzymes enhances purine metabolism distinctly more than does overexpression of enzymes subject to feedback inhibition. Modifications of the sequence of the AgKPR1 gene may be brought about by conventional methods (e.g. Glover, D. M. and Hames, B. D. (1995) DNA cloning Vol. 1, IRL press). It is possible, for example, to exchange the following amino acids of the PRPP synthetase:

The codon which codes for leucine at position 131 can be replaced by a codon which codes for isoleucine. The codon which codes for histidine at position 196 can be replaced by a codon which codes for glutamine.

Figure 2:
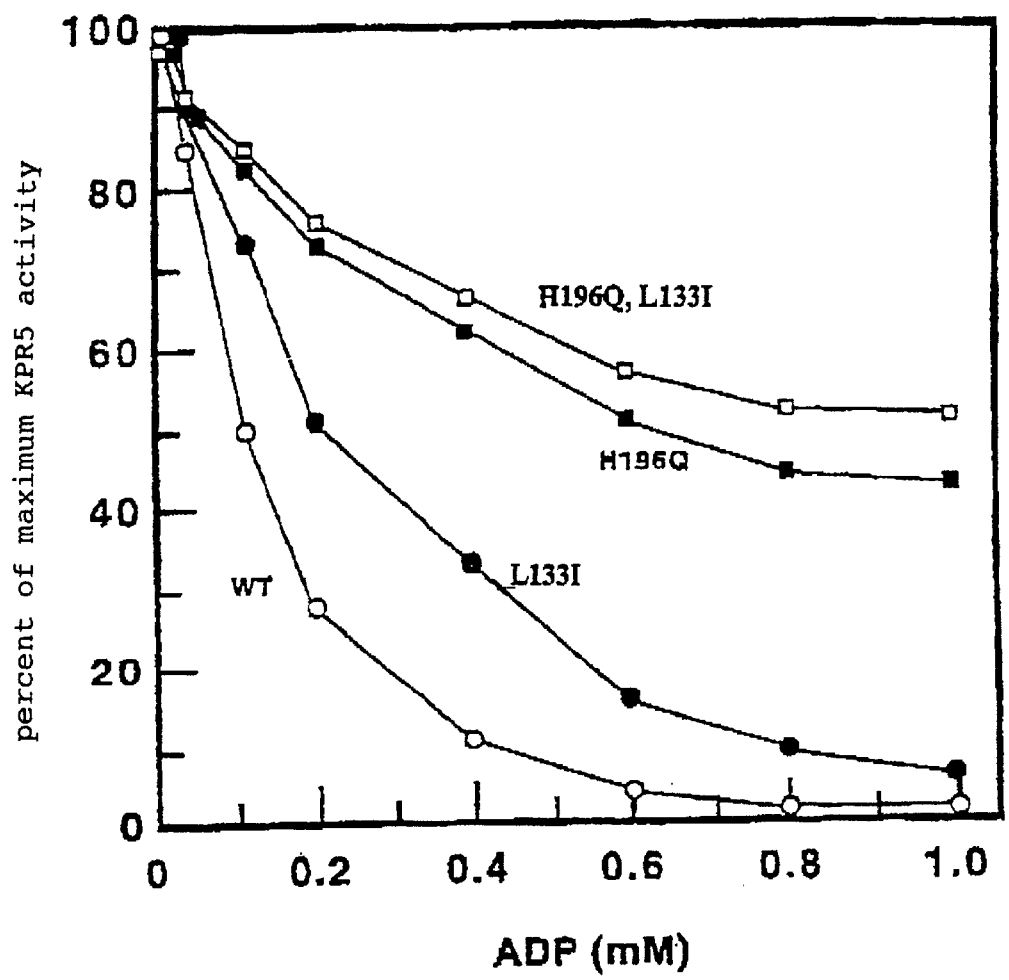

All enzymes which have one of these amino acid exchanges (L131I or H196Q) show a reduced feedback inhibition by purines. FIG. 2 shows this by the example of ADP.

This can be shown after expression of the corresponding enzymes in *Ashbya gossypii*. This can be carried out in accordance with Example 11.

EXAMPLE 14

Variants of the AgGUA1 gene product (IMP dehydrogenase) no longer subject to feedback inhibition by purines or intermediates of purine synthesis.

EXAMPLE 15

Effects of the Enhancement and/or Optimization of Enzymes of Purine Metabolism and Their Genes on Riboflavin Production in *Ashbya gossypii*

The original strain *Ashbya gossypii* ATCC10895 can be tested for riboflavin productivity in shaken flasks, comparing with clones which are derived therefrom and harbor chromosomal copies of genes under the control of the GAP promoter (as described in Example 11). It is possible to use for this purpose 300 ml shaken flasks with 20 ml of YPD medium (Sambrook, J. et al. (1989) Molecular cloning: a laboratory manual, Cold Spring Harbor Laboratory Press), incubating at a temperature of 28° C.

After 2 days, the control strain produces on average 14.5 mg of riboflavin per l of culture broth. Strains which overexpress genes for enzymes of purine metabolism (as shown, for example, in Example 11), or overexpress genes for optimized enzymes of purine metabolism (for example as in Examples 12, 13 and 14), produce more riboflavin. Thus, the strain which overexpresses AgADE4D310VK333A (Example 12) produces on average 45.4 mg of riboflavin per l of culture broth in 2 days.

The strain which overexpresses AgKPR1 with the GAP promoter produces not 14 mj/l (like the WT) but 36 mg/l riboflavin. The strain which overexpresses AgKPR1H196Q with the GAP promoter produces 51 mg/l riboflavin.

FIG. 1:

Measurement of the activity of Gln-PRPP amidotransferase from *A. gossypii* and of modified forms of the enzyme as a function of the concentration of adenosine 5'-monophosphate (AMP) and guanosine 5'-monophosphate (GMP).

WT: Gln-PRPP amidotransferase

A417W: Gln-PRPP amidotransferase, alanine at position 417 replaced by tryptophan.

K333A: Gln-PRPP amidotransferase, lysine at position 333 replaced by alanine.

D310VK333A: Gln-PRPP amidotransferase, aspartate at position 310 replaced by valine and lysine at position 333 replaced by alanine.

FIG. 2:

Measurement of the activity of the PRPP synthetase from *A. gossypii* and of modified forms of the enzyme as a function of the concentration of adenosine 5'-diphosphate (ADP)

WT: PRPP synthetase

L131I: PRPP synthetase, leucine at position 131 replaced by isoleucine

H196Q: PRPP synthetase, histidine at position 196 replaced by glutamine

H196Q, L131I: PRPP synthetase, histidine at position 196 replaced by glutamine and leucine at position 131 replaced by isoleucine

---

We claim:

1. An isolated or purified protein having the polypeptide sequence depicted in SEQ ID NO:5 or a polypeptide sequence obtainable from SEQ ID NO:5 by substitution, insertion or deletion of up to 10% of the amino acids, and having the enzymatic activity of a glutamine-phosphoribosyl-pyrophosphate amidotransferase.

2. A protein whose sequence differs from that set forth in SEQ ID NO:5 in that one or more of the following amino acid substitutions are present: aspartate at position 310 replaced by valine, lysine at position 333 replaced by alanine or alanine at position 417 replaced by tryptophan, wherein said protein has the activity of a glutamine-phosphoribosyl-pyrophosphate amidotransferase.

* * * * *